(12) United States Patent
Antir et al.

(10) Patent No.: US 10,920,176 B2
(45) Date of Patent: Feb. 16, 2021

(54) TRANSPARENT LIQUIDS, IN PARTICULAR FABRIC TREATMENT AGENTS, COMPRISING PERFUME AND MICROCAPSULES WITH AN ODOR MODULATOR COMPOUND

(71) Applicant: Henkel AG & Co. KGaA, Duesseldorf (DE)

(72) Inventors: Marouane Antir, JT Hilversum (DE); Sabine Schuemann, Neuss (DE); Thorsten Bastigkeit, Wuppertal (DE); Luca Bellomi, Duesseldorf (DE); Petra Woltery, Bergisch Gladbach (DE); Frank Sonnenschein, Haan (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 75 days.

(21) Appl. No.: 15/920,673

(22) Filed: Mar. 14, 2018

(65) Prior Publication Data

US 2018/0201883 A1 Jul. 19, 2018

Related U.S. Application Data

(63) Continuation of application No. PCT/EP2016/071899, filed on Sep. 15, 2016.

(30) Foreign Application Priority Data

Sep. 17, 2015 (DE) .................. 10 2015 217 890

(51) Int. Cl.
| | | |
|---|---|---|
| *C11D 17/00* | (2006.01) | |
| *C11D 3/37* | (2006.01) | |
| *C11D 3/20* | (2006.01) | |
| *C11D 3/02* | (2006.01) | |
| *C11D 3/50* | (2006.01) | |
| *A61K 8/49* | (2006.01) | |
| *C11B 9/00* | (2006.01) | |
| *A61K 8/33* | (2006.01) | |
| *A61K 8/35* | (2006.01) | |
| *A61K 8/11* | (2006.01) | |
| *A61K 8/34* | (2006.01) | |
| *A61K 8/37* | (2006.01) | |
| *A61Q 13/00* | (2006.01) | |
| *A61K 8/46* | (2006.01) | |
| *A61K 8/41* | (2006.01) | |
| *C11D 1/83* | (2006.01) | |
| *C11D 3/04* | (2006.01) | |
| *C11D 1/24* | (2006.01) | |
| *C11D 1/29* | (2006.01) | |
| *C11D 1/72* | (2006.01) | |

(52) U.S. Cl.
CPC .............. *C11D 3/505* (2013.01); *A61K 8/11* (2013.01); *A61K 8/33* (2013.01); *A61K 8/347* (2013.01); *A61K 8/35* (2013.01); *A61K 8/37* (2013.01); *A61K 8/41* (2013.01); *A61K 8/46* (2013.01); *A61K 8/49* (2013.01); *A61K 8/494* (2013.01); *A61K 8/4913* (2013.01); *A61K 8/4926* (2013.01); *A61K 8/4973* (2013.01); *A61K 8/4986* (2013.01); *A61Q 13/00* (2013.01); *C11B 9/00* (2013.01); *C11B 9/008* (2013.01); *C11B 9/0015* (2013.01); *C11B 9/0034* (2013.01); *C11B 9/0061* (2013.01); *C11D 1/83* (2013.01); *C11D 3/046* (2013.01); *C11D 3/3765* (2013.01); *A61K 2800/412* (2013.01); *C11D 1/24* (2013.01); *C11D 1/29* (2013.01); *C11D 1/72* (2013.01)

(58) Field of Classification Search
CPC ....... C11D 3/505; C11D 3/046; C11D 3/3765; C11D 1/83; C11D 1/72; C11D 1/24; C11D 1/29; C11B 9/0015; C11B 9/008; C11B 9/0034; C11B 9/0061; C11B 9/00; A61Q 13/00; A61K 8/347; A61K 8/37; A61K 8/46; A61K 8/4913; A61K 8/494; A61K 8/4986; A61K 8/11; A61K 8/33; A61K 8/35; A61K 8/41; A61K 8/49; A61K 8/4926; A61K 8/4973; A61K 2800/412
USPC ................................. 510/337, 276, 109, 108
See application file for complete search history.

(56) References Cited

U.S. PATENT DOCUMENTS

| | | | |
|---|---|---|---|
| 2003/0125222 A1 | 7/2003 | Jahns et al. | |
| 2009/0075857 A1* | 3/2009 | Jonke .................. | C11D 3/3765 510/337 |
| 2011/0217245 A1 | 9/2011 | Derosa et al. | |
| 2012/0308486 A1 | 12/2012 | Singer et al. | |
| 2014/0170102 A1* | 6/2014 | Cetti ....................... | A61K 8/40 424/65 |

FOREIGN PATENT DOCUMENTS

| | | |
|---|---|---|
| DE | 102005015328 A1 | 10/2006 |
| DE | 102008051799 A1 | 4/2010 |
| EP | 0211302 A2 | 2/1987 |

(Continued)

OTHER PUBLICATIONS

PCT International Search Report PCT/EP2016/071899 Completed: Nov. 10, 2016; dated Dec. 12, 2016 6 pages.

*Primary Examiner* — Jessica Whiteley
(74) *Attorney, Agent, or Firm* — Thomas G. Krivulka

(57) ABSTRACT

A liquid, transparent composition comprising microcapsules with at least one odor modulator compound, the composition also comprising at least one perfume. Even though the composition is in capsules, the transparent liquids can be produced using intense and lasting fragrances in the substrate.

15 Claims, No Drawings

(56) References Cited

FOREIGN PATENT DOCUMENTS

| EP | 1976855 A1 | 10/2008 |
| EP | 2087089 A2 | 8/2009 |
| EP | 2087089 B1 | 9/2012 |
| EP | 2687586 A1 | 1/2014 |
| WO | 0149817 A2 | 7/2001 |
| WO | 2007066302 A2 | 6/2007 |

* cited by examiner

TRANSPARENT LIQUIDS, IN PARTICULAR FABRIC TREATMENT AGENTS, COMPRISING PERFUME AND MICROCAPSULES WITH AN ODOR MODULATOR COMPOUND

FIELD OF THE INVENTION

The invention relates to transparent liquids, in particular transparent textile treatment agents, comprising at least one fragrance and microcapsules, in which an odor modulator compound is contained. The invention further relates to a method for providing transparent liquids, in particular transparent textile treatment agents, such as liquid washing agents or liquid softeners.

BACKGROUND OF THE INVENTION

The user associates a sustained experience of fragrance with long-lasting freshness and long-lasting cleanliness. For this reason, the consumer desires perfume compositions that impart a long-lasting fragrance on a substrate. In order to make it possible to fragrance a substrate over a longer period of time, the prior art discloses various methods for prolonging the experience of fragrance and methods for delaying the release of fragrances.

For example, European patent EP 1 976 855 B1 describes oxazolidines, which are used as fragrance precursors and release an odorant by slow hydrolysis, thus generating a long-lasting fragrance.

European patent EP 2 087 089 B1 describes the use of perfume microcapsules as a deposition system, the capsules breaking open at a specified time and providing a short, relatively intense fragrance.

In particular the use of encapsulated fragrances has proven valuable for fragrancing substrates, in particular textile surfaces. The encapsulated fragrances deposit on the surface, in particular on and between the fibers of the textile surface, and can release the fragrance by diffusion of the fragrance from the capsule or by mechanically causing the capsule to rupture.

It has also been found that the consumer regards transparent, liquid compositions as aesthetically pleasing. However, providing a transparent, liquid composition having an encapsulated perfume in the form of suspended particles is challenging. Firstly, in order to adequately and long-lastingly fragrance a substrate, the composition has to contain a sufficient amount of suspended fragrance capsules. Secondly, the amount of the fragrance capsules should not be too high as the liquid will otherwise become clouded. Liquid compositions that contain the minimum amount of perfume-comprising microcapsules required to sufficiently long-lastingly fragrance substrates have not previously been sufficiently transparent. The applies even more so to the provision of transparent, liquid compositions in the form a microcapsule concentrate.

BRIEF SUMMARY OF THE INVENTION

The object of the present invention was to improve the transparency of liquid compositions that contain microcapsules in order to prolong fragrance. At the same time, according to the use of said transparent composition on a substrate, in particular within the scope of textile treatment, it is intended for an adequate, long-lasting and intense fragrancing of the substrate to be achieved. It is further intended for it to be possible to provide the composition according to the invention with any desired, but specific fragrance profile that has a long-lasting high fragrance intensity. It is also intended to be made possible to provide transparent, liquid fragrance compositions as a microcapsule concentrate, for example within the scope of providing transparent liquid washing agent concentrates or softener concentrates.

A first subject of the invention for solving said problem is a liquid, transparent composition, in particular as a textile treatment agent, comprising
    a) at least one odorant and
    b) from 0.00001 to 0.2 wt. % microcapsules, comprising at least one odor modulator compound, wherein each individual modulator compound
        i) is contained, based on the total of all the odorants contained in the composition, in an amount of from 2 wt. % to 0.000001 wt. %, and
        ii) contains at least one heteroatom, wherein the at least one heteroatom is selected from N, O, S, Si, Se, F, Cl, Br or I, and
        iii) has a molecular weight of lower than 250 g mol$^{-1}$, and wherein the composition has an efficiency factor of at least 1.15 on account of the at least one odor modulator compound, wherein the efficiency factor is calculated according to the following formula:

$$E = \frac{P_{GMV}}{P+1} \geq 1.15$$

where E=efficiency factor and P=number of persons trained in odors that deemed the composition having an odor modulator compound ($P_{GMV}$) or not having an odor modulator compound (P) to be more intense, wherein the sum of $P_{GMV}$ and P is at least 34.

It has surprisingly been found that the fragrance intensity of a liquid composition according to the invention, comprising the microcapsules having at least one odor modulator compound and at least one odorant, is higher not only initially, but in particular also long-lastingly in comparison with a conventional perfume oil and conventional perfume microcapsules. The fact that the effect achieved by at least one non-encapsulated odor modulator compound was again significantly enhanced by the use of at least one micro-encapsulated odor modulator compound was particularly surprising. In the process, effects were achieved which generally even exceed the sum of the individual effects that are achieved by micro-encapsulating at least one odorant and by adding at least one odor modulator compound to a perfume oil, i.e. which have a synergistic effect. On account of the achieved effects, it is therefore possible to significantly decrease the amount of odorants in the composition according to the invention, without thereby lowering the intensity of the fragrance in comparison with a conventional perfume composition or substantially changing the fragrance profile of the perfume composition. It is possible to produce liquid compositions for long-lastingly fragrancing that are transparent.

Furthermore, a perfume composition according to the invention, on account of the lower amount that is required to achieve the same fragrance intensity as a conventional perfume composition, can be stably incorporated into a typical, in particular liquid, consumer product or a highly-concentrated consumer product.

Furthermore, suspensions of optical effect solids, e.g. pearlescing pigments, speckles or color pigments, demonstrate a particularly effective optical effect if the transparent, liquid composition according to the invention is used to suspend said optical effect solids as a continuous phase.

These and other features and advantages of the invention will become apparent to a person skilled in the art upon studying the following detailed description and claims. It will readily be understood that the examples contained herein are intended to describe and illustrate but not to limit the invention and that, in particular, the invention is not limited to these examples.

According to the definition of the invention, a substance (e.g. a composition) is in the form of a solid if it is in the solid physical state at 25° C. and 1013 mbar.

According to the definition of the invention, a substance (e.g. a composition) is liquid if it is in the liquid physical state at 25° C. and 1013 mbar.

A chemical compound is an organic compound if the molecule of the chemical compound contains at least one covalent bond between carbon and hydrogen.

By contrast with the definition of an organic compound, a chemical compound is an inorganic compound if the molecule of the chemical compound does not contain a covalent bond between carbon and hydrogen.

The transparency of the liquid composition according to the invention may be determined by various methods. The Nephelometric Turbidity Unit (NTU) is often used as a measurement value for transparency. Said unit, used e.g. in water treatment, is for turbidity measurements in liquids. Said unit describes the turbidity of a liquid measured using a calibrated nephelometer. High NTU values are measured for cloudy liquids, whereas low values are determined for clear, transparent liquids.

The HACH Turbidimeter 2100Q from Hach Company, Loveland, Colo. (USA) was used with StablCal Solution HACH (20 NTU), StablCal Solution HACH (100 NTU) and StablCal Solution HACH (800 NTU) being used as calibrating substances, all of which can also be ordered from Hach Company. For the measurement, a 10 ml measuring cuvette having a cap was filled with the composition to be examined, and the measurement was carried out at 20° C.

Within the meaning of the invention, at a NTU value (at 20° C.) of 60 or more, liquids have a turbidity that is perceived as unaesthetic for a transparent composition, as far as can be detected by the naked eye.

Within the scope of the present invention, the transparency of the agents according to the invention was determined by a transparency measurement at 500 nm and 20° C. For this purpose, the sample is measured in an optical waveguide photometer (Metrohm 662 having a turbidity sensor) having an optical waveguide measuring cell of which the mirror is unscrewed at a light path of 2×10 mm, and having a Wolfram lamp (3.9 watt) as a light source.

If an agent has, at 500 nm, a transmission of 55%, it is considered to be transparent within the meaning of the invention. It is preferred for the agent according to the invention to have a transmission of 60%, particularly preferably 70%, very particularly preferably 80%.

Microcapsules within the meaning of the present invention include any kind of capsule known to a person skilled in the art, though in particular core/shell capsules and matrix capsules. Matrix capsules are porous shaped bodies that have a structure similar to a sponge. Core/shell capsules are shaped bodies that have a core and a shell. Suitable microcapsules are capsules that have an average diameter $X_{50.3}$ (volume average) of from 0.1 to 200 µm, preferably from 1 to 100 µm, more preferably from 5 to 80 µm, particularly preferably from 10 to 50 µm, and in particular from 15 to 40 µm. The average of particle size diameter $X_{50.3}$ is determined by sieving or by means of a Camsizer particle size analyzer from Retsch.

The terms "microcapsule" and "capsule" are used synonymously within the meaning of the present invention.

Unless indicated otherwise, all percentages indicated are percent by weight (wt. %). Unless indicated otherwise, stated amounts of components of the compositions described herein always relate to the amount of the pure component. Moreover, state amounts that relate to at least one component always denote the total amount of this type of component contained in the composition, unless explicitly indicated otherwise.

Numerical ranges that are given in the format "from x to y" include the cited values. If several preferred numerical ranges are indicated in this format, it is self-evident that all ranges that result from the combination of the various endpoints are also included.

"At least one", as used herein, refers to one or more, for example 2, 3, 4, 5, 6, 7, 8, 9 or more. In connection with components of the perfume compositions described herein, this information does not refer to the absolute amount of molecules, but to the type of the component. "At least one odor modulator compound" therefore signifies, for example, one or more different odor modulator compounds, i.e. one or more different types of odor modulator compounds. Together with stated amounts, the stated amounts refer to the total amount of the correspondingly designated type of component, unless indicated otherwise.

All features that relate, for example, to "at least one odor modulator compound" or "at least one odorant", e.g. the odor detection threshold, stated amounts or ratios, apply to each individual odor modulator compound or each individual odorant, respectively, and so on. Therefore, if two odor modulator compounds/odorants are contained in the perfume composition in a specific amount range, for example, this means that the first odor modulator compound or the first odorant is contained in the specific amount range, and the second odor modulator compound/the second odorant is contained in the specific amount range.

A composition within the meaning of the present invention comprises at least one odorant that contributes substantially to the achievement of a specific fragrance profile. An odorant within the meaning of the invention may be in the form of an odorant precursor or as a free odorant.

A perfume oil within the meaning of the present invention is a combination of various odorants and optionally solvents that produce a specific fragrance profile. A perfume oil may also contain odor modulator compounds. A perfume oil comprises in particular no micro-encapsulated odorants or micro-encapsulated odor modulator compounds.

The terms "odorant" and "fragrance" are used synonymously within the meaning of the present invention. An odorant is a compound that has a characteristic odor and contributes to the achievement of a specific fragrance profile of a perfume composition or of a perfume oil. Odorants also include compounds that change the fragrance profile of a perfume composition to the effect that the fragrance takes on a particular depth, which is typically known to a person skilled in the art as the complexity of a fragrance. An odorant within the meaning of the present invention does not have, however, a direct influence on the fragrance intensity of the perfume composition, as long as the perfume composition is used at a constant concentration.

The fragrance profile of a composition or of a perfume oil is the specific fragrance that a user perceives on account of the contained odorants. Without being limited hereto in any way, a fragrance may smell, for example, flowery, spicy, sweet, sour, bitter, fresh, woody, fruity, leathery, oriental, like animals, like chypre, like fougere, citric, edible, green, musky, like ozone, aldehydic, like citrus fruits, aromatic or marine; complex fragrance profile can be achieved by specifically selecting the individual odorants in the perfume composition or the perfume oil, and a flowery fragrance may smell, for example, like roses, violets or lavender. A fragrance profile is therefore the characteristic fragrance of each composition or of each perfume oil that is produced as a result of the odorants used.

An odor modulator compound (OMC) within the meaning of the present invention is a compound which, while it may have its own odor, does not contribute or substantially contribute, in the concentration used and under the test conditions indicated below, to a change in the fragrance profile of the composition, comprising at least one odorant and microcapsules having at least one odor modulator compound. A negligible change in the fragrance profile of the composition means that, while the fragrance profile may deviate slightly from the original fragrance profile of the perfume composition, a person skilled in the art nevertheless still recognizes said profile as the original fragrance profile. However, an odor modulator compound within the meaning of the present invention, in spite of the low concentration thereof used, has a substantial influence on the fragrance intensity of the composition according to the invention perceived by the user, and therefore, for example, a lower amount of the perfume composition can be used to achieve the same fragrance intensity than in the case of a conventional perfume composition not having microcapsules or an odor modulator compound. In contrast with an odorant contained in a perfume composition, an odor modulator compound does not therefore define the fragrance profile, but rather increases the fragrance intensity of the fragrance profile of the perfume composition defined by the odorants. Since the at least one odor modulator compound does not substantially change the fragrance profile of the perfume composition, in principle any desired fragrance profile may be implemented without objectionable secondary notes being perceived.

An odor modulator compound increases the fragrance intensity of the composition according to the invention, and this is described by the efficiency factor (E). The efficiency factor is a measure for the fragrance intensity of two compositions comprising identical odorant combinations, one of the two perfume compositions additionally comprising at least one odor modulator compound within the meaning of the present invention. A group of at least 34 persons trained in odors assesses the intensity of the two perfume compositions and decides on the perfume composition which has a more intense smell than the other, the intensity of the perfume compositions within the scope of the embodiments of this invention being assessed by exactly 34 persons trained in odors. Subsequently, the number of persons trained in odors that deemed the perfume composition having an odor modulator compound to be more intense ($P_{GMV}$) is divided by the number of persons trained in odors that deemed the perfume composition not having an odor modulator compound to be more intense (P), according to formula $$E = \frac{P_{GMV}}{P+1} \geq 1.15$$

The efficiency factor (E) is obtained as a result. An odor modulator compound increases the fragrance intensity of the perfume composition according to the invention such that the efficiency factor has at least a value of 1.15. In a preferred embodiment, the efficiency factor has at least a value of 1.5, more preferably a value of at least 1.75, or even more preferably a value of at least 2.

In a preferred embodiment of the invention, the composition according to the invention contains at least one odor modulator compound selected from 2-acetylpyridine (CAS no. 1122-62-9), 2,5-dimethylpyrazine (CAS no. 123-32-0), ethyl 3-methylthiopropionate (CAS no. 13327-56-5), methyl 3-methylthiopropionate (CAS no. 13532-18-8), 2,3,5-trimethylpyrazine (CAS no. 14667-55-1), 2-ethyl-4-methylthiazole (CAS no. 15679-12-6), 2-isopropyl-4-methylthiazole (CAS no. 15679-13-7), 2-ethyl-3-methylpyrazine (CAS no. 15707-23-0), 2-isobutylthiazole (CAS no. 18640-74-9), ethyl 2-mercaptopropionate (CAS no. 19788-49-9), 2-acetylpyrazine (CAS no. 22047-25-2), 4-methylthio-4-methylpentan-2-one (CAS no. 23550-40-5), 2-acetyl-3-methylpyrazine (CAS no. 23787-80-6), 2-acetylthiazole (CAS no. 24295-03-2), S-methyl butanethioate (CAS no. 2432-51-1), 2-isobutyl-3-methoxypyrazine (CAS no. 24683-00-9), 2,2'-(dithiodimethylene)difuran (CAS no. 4437-20-1), 3-methylthio-1-hexanol (CAS no. 51755-66-9), 3-mercapto-1-hexanol (CAS no. 51755-83-0), dibutyl sulfide (CAS no. 544-40-1), 2,3-dimethylpyrazine (CAS no. 5910-89-4), 1-para-menthene-8-thiol (CAS no. 71159-90-5), 2-mercaptopropionic acid (CAS no. 79-42-5), 2,2,4,4,6,6-hexamethyl-1,3,5-trithiane (CAS no. 828-26-2), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), methyl corylone (CAS no. 13494-06-9), sotolone (CAS no. 28664-35-9), furaneol methyl ether (CAS no. 4077-47-8), emoxyfurone (CAS no. 698-10-2), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), sulfurol (CAS no. 137-00-8), benzothiazole (CAS no. 95-16-9), 4,5-dihydro-3(2H)thiophenone (CAS no. 1003-04-9), 2-hydroxy-2-cyclohexen-1-one (CAS no. 10316-66-2), 3-acetyl-2,5-dimethylfuran (CAS no. 10599-70-9), 2-propionylpyrrol (CAS no. 1073-26-3), 2-(methylthio)phenol (CAS no. 1073-29-6), methyl 2-furfurylthioacetate (CAS no. 108499-33-8), furfurylideneacetone (CAS no. 108811-61-6), natural pyrazine mixture (CAS no. 84082-50-8), 1-pentanethiol (CAS no. 110-66-7), 2-methoxycinnamyl acetate (CAS no. 110823-66-0), dipropyl sulfide (CAS no. 111-47-7), 2,3,5,6-tetramethylpyrazine (CAS no. 1124-11-4), 2-hexylpyridine (CAS no. 1129-69-7), 4-butyroxy-2,5-dimethyl-3(2H)-furanone (CAS no. 114099-96-6), 2,6-dimethylthiophenol (CAS no. 118-72-9), 2-methylheptanoic acid (CAS no. 1188-02-9), 1,6-hexanedithiol (CAS no. 1191-43-1), 2-acetylfuran (CAS no. 1192-62-7), 2-acetyl-5-methylfuran (CAS no. 1193-79-9), 2,4,5-trimethylthiazole (CAS no. 13623-11-5), 1-(methylthio)-2-butanone (CAS no. 13678-58-5), 2-methyl-5-thiomethylfuran (CAS no. 13678-59-6), furfuryl thioacetate (CAS no. 13678-68-7), 3-thiohexylacetate (CAS no. 136954-20-6), 3-mercaptohexylbutyrate (CAS no. 136954-21-7), 3-mercaptohexylhexanoate (CAS no. 136954-22-8), 3-acetylthiohexylacetate (CAS no. 136954-25-1), 2-thiocresol (CAS no. 137-06-4), 2-ethylpyrazine (CAS no. 13925-00-3), 1-methylthio-2-propanone (CAS no. 14109-72-9), 3-(2-methylpropyl)pyridine (CAS no. 14159-61-6), furfuryl methyl sulfide (CAS no. 1438-91-1), 1-(2-furanylmethyl)-1H-pyrrole (CAS no. 1438-94-4), 2-butylthiophene (CAS no. 1455-20-5), S-methyl thioacetate (CAS no. 1534-08-3), 2,3-diethylpyrazine (CAS no. 15707-24-1), 2-methyl-3-propylpyrazine (CAS no. 15986-80-8), 2,3-dihydro-5,6-dimethylpyrazine (CAS no. 15986-92-2), bis-(methylthio)methane (CAS no. 1618-26-4), 3-methylthiobutanal (CAS no. 16630-52-7), 3-(methylthio)propylacetate (CAS no. 16630-55-0), 3-(methylthio)propylbutyrate (CAS no. 16630-60-7), methyl (methylthio)acetate (CAS no. 16630-66-3), 4-methyl-5-vinylthiazole (CAS no. 1759-28-0), 2,3-diethyl-5-methylpyrazine (CAS no. 18138-04-0), 2-(1-methylpropyl)thiazole (CAS no. 18277-27-5), 2-methylbutane-1-thiol (CAS no. 1878-18-8), 2-hexylthiophene (CAS no. 18794-77-9), furfuryl isopropyl sulfide (CAS no. 1883-78-9), 4-methyl-4-mercapto-pentan-2-one (CAS no. 19872-52-7), ethyl methyl disulfide (CAS no. 20333-39-5), diallyl trisulfide (CAS no. 2050-87-5), 4-methylthiobutanol (CAS no. 20582-85-8), 2,4,5-trimethyloxazole (CAS no. 20662-84-4), 3-methyl-2-butanethiole (CAS no. 2084-18-6), 2-pentanethiol (CAS no. 2084-19-7), 2-(3-phenylpropyl)pyridine (CAS no. 2110-18-1), diallyl disulfide (CAS no. 2179-57-9), allyl methyl sulfide (CAS no. 2179-58-0), allyl propyl disulfide (CAS no. 2179-59-1), 2,3-dithiahexane (CAS no. 2179-60-4), 2,4,5-trimethyl-3-oxazoline (CAS no. 22694-96-8), 2-pentylpyridine (CAS no. 2294-76-0), 2-methylthioacetaldehyde (CAS no. 23328-62-3), 2-methyl-2-thiazoline (CAS no. 2346-00-1), 3,5-dimethyl-1,2,4-trithiolane (CAS no. 23654-92-4), 5-methyl-6,7-dihydrocyclopentapyrazine (CAS no. 23747-48-0), 2-methylthiazolidine (CAS no. 24050-16-6), 2-methyltetrahydrofuran-3-thioacetate (CAS no. 252736-41-7), 2-methyl-3-furanthiol (CAS no. 2858874-1), bis-(2-methyl-3-tetrahydrofuran)disulfide (CAS no. 28588-75-2), 3-methylcyclohexan-1,2-dione (CAS no. 3008-43-3), ethyl propyl disulfide (CAS no. 30453-31-7), 3(5-methyl-2-furyl)butanal (CAS no. 31704-80-0), 2-methyltetrahydrofuran-3-one (CAS no. 3188-00-9), 2-pentanoylfuran (CAS no. 3194-17-0), 2-ethylfuran (CAS no. 3208-16-0), 3-methylthiopropanal (CAS no. 3268-49-3), 2-acetyl-3-ethylpyrazine (CAS no. 32974-92-8), 4-(methylthio)-2-butanone (CAS no. 34047-39-7), 3-acetylpyridine (CAS no. 350-03-8), 2-pyrazineethanethiol (CAS no. 35250-53-4), 4,5-dimethylthiazole (CAS no. 3581-91-7), 2-pentylfuran (CAS no. 3777-69-3), 2-heptylfuran (CAS no. 3777-71-7), 5-acetyl-2,4-dimethylthiazole (CAS no. 38205-60-6), 3-methylthiohexanal (CAS no. 38433-74-8), thiogeraniol (CAS no. 39067-80-6), 2-ethyl-5-methylthiophene (CAS no. 40323-88-4), 3-mercapto-2-butanone (CAS no. 40789-98-8), 3-methylthiopropylamine (CAS no. 4104-45-4), 4-acetoxy-2,5-dimethyl-3(2H)-furanone (CAS no. 4166-20-5), S-methyl-2-methylbutanthioate (CAS no. 42075-45-6), 2-propylfuran (CAS no. 4229-91-8), diisopropyl disulfide (CAS no. 4253-89-8), 2-propionylthiazole (CAS no. 43039-98-1), 2-phenylethanethiol (CAS no. 4410-99-5), ethyl 2-(methylthio)acetate (CAS no. 4455-13-4), 2-butylfuran (CAS no. 4466-24-4), 2-ethylthiophenol (CAS no. 4500-58-7), 2-pentylthiophene (CAS no. 4861-58-9), ethyl 2-methyl-2-methylthiopropionate (CAS no. 49773-24-2), 2-(ethylthio)-1-propanol (CAS no. 72311-96-7), 3-methylthiopropanol (CAS no. 505-10-2), 3-methylthiopropylisothiocyanate (CAS no. 505-79-3), thioacetic acid (CAS no. 507-09-5), methyl 2-(methylthio)butyrate (CAS no. 51534-66-8), 3-methylthio-hex-1-ylacetate (CAS no. 51755-85-2), 2-(methylthio)ethanol (CAS no. 5271-38-5), methyl 4-methylthiobutyrate (CAS no. 53053-51-3), 2-isobutyl-4,5-dimethylthiazole (CAS no. 53498-32-1), 3-ethylpyridine (CAS no. 536-78-7), 2-ethyl-4,5-dimethyloxazole (CAS no. 53833-30-0), 2,4-dimethylthiazole (CAS no. 541-58-2), 2-butyl-5-ethylthiophene (CAS no. 54411-06-2), 2,4,6-triethyldihydro-1,3,5-dithiazine (CAS no. 54717-17-8), 3-mercapto-2-butanol (CAS no. 54812-86-1), 2-ethyl-3 (5/6)-dimethylpyrazine (CAS no. 55031-15-7), 2-methyl-1,3-dithiolane (CAS no. 5616-51-3), 2-methyltetrahydrofuran-3-thiol (CAS no. 57124-87-5), 3,5,5-trimethylcyclohexane-1,2-dione (CAS no. 57696-89-6), 1.2-cyclohexanediol (CAS no. 57794-08-8), furfuryl thiopropionate (CAS no. 59020-85-8), furfuryl thioformate (CAS no. 59020-90-5), dipropyl trisulfide (CAS no. 6028-61-1), S-methyl-4-methyl pentanethioate (CAS no. 61122-71-2), 5-methylfurfural (CAS no. 620-02-0), 2-propylpyridine (CAS no. 622-39-9), furfuryl acetate (CAS no. 62317-6), 3-(2-furyl)acrolein (CAS no. 623-30-3), dimethyl disulfide (CAS no. 624-92-0), ethyl thioacetate (CAS no. 625-60-5), 2-thienylmercaptan (CAS no. 6258-63-5), 1-phenylethanethiol (CAS no. 6263-65-6), n-butyl methyl sulfide (CAS no. 628-29-5), dipropyl disulfide (CAS no. 629-19-6), 2-isobutylpyridine (CAS no. 6304-24-1), 2,5-dimethylthiophene (CAS no. 638-02-8), 2,4,6-trithiaheptane (CAS no. 6540-86-9), 4-methyl-5-thiazolethanolacetate (CAS no. 656-53-1), 2-(sec-butyl)-4,5-dimethyl-3-thiazoline (CAS no. 65894-82-8), 2-isobutyl-4,5-dimethyl-3-thiazoline (CAS no. 65894-83-9), 4-allyl-2,6-dimethoxyphenol (CAS no. 6627-88-9), 3-mercapto-2-pentanone (CAS no. 67633-97-0), 2-methyl-4-propyl-1,3-oxathiane (CAS no. 59323-76-1), 2-methylthio-3(5/6) methylpyrazine (CAS no. 67952-65-2), 4-methylthiazole (CAS no. 693-95-8), 2-furyl-2-propanone (CAS no. 6975-60-6), benzyl methyl disulfide (CAS no. 699-10-5), amyl methyl disulfide (CAS no. 72437-68-4), 2-methylquinoxaline (CAS no. 7251-61-8), 2-acetyl-3,5(6)-dimethylpyrazine (CAS no. 72797-17-2), diallyl polysulfide (CAS no. 72869-75-1), ethyl-2-methoxybenzoate (CAS no. 7335-26-4), methyl thiomethyl hexanoate (CAS no. 74758-91-1), methyl thiomethyl butyrate (CAS no. 74758-93-3), methyl mercaptan (CAS no. 74-93-1), benzyl methyl sulfide (CAS no. 766-92-7), 2-ethyl-4,5-dimethylthiazoline (CAS no. 76788-46-0), 2-methoxy-4-vinylphenol (CAS no. 7786-61-0), allyl mercaptan (CAS no. 870-23-5), 2-methyl-3-(2-furyl)prop-2-enal (CAS no. 874-66-8), 2-octylthiophene (CAS no. 880-36-4), 1,5-pentanedithiol (CAS no. 928-98-3), isoamyl 3-methylthiopropionate (CAS no. 93762-35-7), ethyl 3-(furfurylthiol)propionate (CAS no. 94278-27-0), para-mentha-8-thioacetat-3-one (CAS no. 94293-57-9), furfuryl alcohol (CAS no. 98-00-0), 3-acetyl-2,5-dimethylthiophene (CAS no. 2530-10-1), ethyl 2-methylbutyrate (CAS no. 7452-79-1), decenal-4-trans (CAS no. 65405-70-1).

In a particularly preferred embodiment of the invention, the composition according to the invention composition contains at least one odor modulator compound selected from 2-acetylpyridine (CAS no. 1122-62-9), 2,5-dimethylpyrazine (CAS no. 123-32-0), ethyl 3-methylthiopropionate (CAS no. 13327-56-5), methyl 3-methylthiopropionate (CAS no. 13532-18-8), 2,3,5-trimethylpyrazine (CAS no. 14667-55-1), 2-ethyl-4-methylthiazole (CAS no. 15679-12-6), 2-isopropyl-4-methylthiazole (CAS no. 15679-13-7), 2-ethyl-3-methylpyrazine (CAS no. 15707-23-0), 2-isobutylthiazole (CAS no. 1864074-9), ethyl 2-mercaptopropionate (CAS no. 19788-49-9), 2-acetylpyrazine (CAS no. 22047-25-2), 4-methylthio-4-methylpentan-2-one (CAS no. 23550-40-5), 2-acetyl-3-methylpyrazine (CAS no. 2378780-6), 2-acetylthiazole (CAS no. 24295-03-2), S-methyl butanethioate (CAS no. 2432-51-1), 2-isobutyl-3-methoxypyrazine (CAS no. 24683-00-9), 2,2'-(dithiodimethylene)difuran (CAS no. 4437-20-1), 3-methylthio-1-hexanol (CAS no. 51755-66-9), 3-mercapto-1-hexanol (CAS no. 51755-83-0), dibutyl sulfide (CAS no. 544-40-1), 2,3-dimethylpyrazine (CAS no. 5910-89-4), 1-para-menthene-8-thiol (CAS no. 71159-90-5), 2,2,4,4,6,6-hexamethyl-1,3,5-trithiane (CAS no. 828-26-2), furfuryl mercaptan (CAS no. 98-02-2), menthofuran (CAS no. 494-90-6), homofuranol (CAS no. 27538-09-6), furaneol (CAS no. 3658-77-3), 1-(2-Benzofuranyl)ethanone (CAS no. 1646-26-0), nerolione (CAS no. 23911-56-0), methyl corylone (CAS no. 13494-06-9), sotolone (CAS no. 28664-35-9), furaneol methyl ether (CAS no. 4077-47-8), emoxyfurone (CAS no. 698-10-2), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), sulfurol (CAS no. 137-00-8), benzothiazole (CAS no. 95-16-9), ethyl 2-methylbutyrate (CAS no. 7452-79-1), decenal-4-trans (CAS no. 65405-70-1).

Although the indicated names of the odor modulator compounds within the present application are clear in principle, and a person skilled in the art would not have any problems in identifying the corresponding substances, the CAS numbers of the odor modulator compounds have been indicated for simplification. If the indicated name unexpectedly does not match the indicated CAS number, the CAS number shall apply in case of doubt. Only in cases where it is obvious that the CAS number is incorrect should the name indicated for that CAS number be preferred. This rule also applies to all other compounds within the present application for which both a systematic or trivial name and a CAS number are indicated.

In a preferred embodiment of the invention, the at least one odor modulator compound is an odor modulator compound of general formula (I),

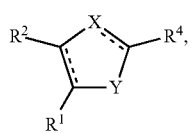

Formula (I)

where
X represents nitrogen, sulfur or $CR^3$; and
Y represents oxygen, sulfur or $NR^5$; and
$R^1$, $R^2$ and $R^5$ each represent, independently of one another, hydrogen or functional groups having 1 to 6 carbon atoms; and
$R^3$ and $R^4$ each represent, independently of one another, hydrogen or functional groups having 1 to 9 carbon atoms,
where
the ring of formula (I) may contain, at the positions linked by dashed lines, each independently of one another, double bonds, with the proviso that the at least one odor modulator compound, if X represents nitrogen, contains a double bond between X and the carbon atom of the ring of formula (I) that is linked to $R^4$; and the carbon atoms of the ring of formula (I) that are linked to $R^1$ and $R^2$ may together be part of an annulated five-member or six-member ring, where functional groups $R^1$ and $R^2$ are each, independently of one another, an integral part of the annulated ring either completely or in part;
and
one or more methyl groups, methylene groups, methine groups or quaternary carbon atoms of functional groups $R^1$ to $R^5$ may each, independently of one another, be substituted by heteroatoms.

Within the meaning of this embodiment, in the ring of general formula (I) the positions linked by dashed lines may each, independently of one another, comprise double bonds. However, double bonds are in particular not present if the natural valences of the atoms involved in the double bond are already saturated as a result of the selection of X or functional groups $R^1$ to $R^4$. This means that the atoms involved in the double bond in principle have to be uncharged. If X, for example, is sulfur, the bond between X and the carbon atom that is directly linked to $R^4$ cannot be a double bond. Even if one of functional groups $R^1$ to $R^4$ forms a double bond to one of the carbon atoms in the ring of general formula (I), the corresponding atom in the ring can no longer be involved in a double bond within the ring.

Within the meaning of this embodiment, the carbon atoms of the ring of formula (I) that are linked to $R^1$ and $R^2$ may together be part of an annulated five-member or six-member ring, where functional groups $R^1$ and $R^2$ are each, independently of one another, an integral part of the annulated ring either completely or in part. In this context, "annulated" means that two carbon rings share a carbon-to-carbon bond, specifically the carbon atoms of the ring of formula (I) that are linked to $R^1$ and $R^2$, it being possible for said bond to be a single or double bond. If functional groups $R^1$ and $R^2$ are only in part an integral part of the annulated ring, the non-integral parts of the ring of the ring of functional groups $R^1$ and $R^2$ may, for example, be in the form of a side chain of the annulated ring.

The at least one odor modulator compound of general formula (I) preferably contains one to four heteroatoms, selected from the group of nitrogen, oxygen or sulfur.

Preferred functional groups $R^1$ to $R^5$ in general formula (I) are, for example, alkyl groups, alkenyl groups, aryl groups, hydroxy groups, alkanol groups, acyl groups, (alkyl) ester groups, (alkyl) thiol groups, thioether groups and (alkyl) aldehyde groups. In principle, the various functional groups may be contained in functional groups $R^1$ to $R^5$ in any desired combination; however, within the meaning of this embodiment, it is preferred, if Y=nitrogen and X=$CR^3$, for functional groups $R^1$ and $R^2$ to not be completely or in part an integral part of the six-member ring.

In a preferred embodiment of invention, the at least one odor modulator compound of general formula (I) is selected from 2-ethyl-4-methylthiazole (CAS no. 15679-12-6), 2-isopropyl-4-methylthiazole (CAS no. 15679-13-7), 2-isobutylthiazole (CAS no. 18640-74-9), 2-acetylthiazole (CAS no. 24295-03-2), 2,2'-(dithiodimethylene)difuran (CAS no. 4437-20-1), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), furfural propylene glycol acetal (CAS no. 4359-54-0), furaneol methyl ether (CAS no. 4077-47-8), sulfurol (CAS no. 137-00-8), benzothiazole (CAS no. 95-16-9), 4.5-dihydro-3(2H)thiophenone (CAS no. 100304-9), 3-acetyl-2,5-dimethylfuran (CAS no. 10599-70-9), 2-propionylpyrrole (CAS no. 1073-26-3), methyl 2-furfurylthioacetate (CAS no. 108499-33-8), furfurylideneacetone (CAS no. 108811-61-6), 4-butyroxy-2,5-dimethyl-3(2H)-furanone (CAS no. 114099-96-6), 2-acetylfuran (CAS no. 1192-62-7), 2-acetyl-5-methylfuran (CAS no. 1193-79-9), 2,4,5-trimethylthiazole (CAS no. 13623-11-5), 2-methyl-5-thiomethylfuran (CAS no. 13678-59-6), furfuryl thioacetate (CAS no. 13678-68-7), furfuryl methyl sulfide (CAS no. 1438-91-1), 1-(2-furanylmethyl)-1H-pyrrole (CAS no. 1438-94-4), 2-butylthiophene (CAS no. 1455-20-5), 4-methyl-5-vinylthiazole (CAS no. 1759-28-0), 2-(1-methylpropyl)thiazole (CAS no. 18277-27-5), 2-hexylthiophene (CAS no. 18794-77-9), furfuryl isopropyl sulfide (CAS no. 1883-78-9), 2,4,5-trimethyloxazole (CAS no. 20662-84-4), 2-methyl-2-thiazoline (CAS no. 2346-00-1), 2-methylthiazolidine (CAS no. 24050-16-6), 2-methyltetrahydrofuran-3-thioacetate (CAS no. 252736-41-7), 2-methyl-3-furanthiol (CAS no. 2858874-1), bis-(2-methyl-3-tetrahydrofuran)disulfide (CAS no. 28588-75-2), 3(5-methyl-2-furyl)butanal (CAS no. 31704-80-0), 2-methyltetrahydrofuran-3-one (CAS no. 3188-00-9), 2-pentanoylfuran (CAS no. 3194-17-0), 2-ethylfuran (CAS no. 3208-16-0), 4,5-dimethylthiazole (CAS no. 3581-91-7), 2-pentylfuran (CAS no. 3777-69-3), 2-heptylfuran (CAS no. 3777-71-7), 5-acetyl-2,4-dimethylthiazole (CAS no. 38205-60-6), 2-ethyl-5-methylthiophene (CAS no. 40323-88-4), 4-acetoxy-2,5-dimethyl-3 (2H)-furanone (CAS no. 4166-20-5), 2-propylfuran (CAS no. 4229-91-8), 2-propionylthiazole (CAS no. 43039-98-1), 2-butylfuran (CAS no. 4466-24-4), 2-pentylthiophene (CAS no. 4861-58-9), 2-isobutyl-4,5-dimethylthiazole (CAS no. 53498-32-1), 2-ethyl-4,5-dimethyloxazol (CAS no. 53833-30-0), 2,4-dimethylthiazole (CAS no. 541-58-2), 2-butyl-5-ethylthiophene (CAS no. 54411-06-2), 2-methyl-1,3-dithiolane (CAS no. 5616-51-3), 2-methyltetrahydrofuran-3-thiol (CAS no. 57124-87-5), furfuryl thiopropionate (CAS no. 59020-85-8), furfuryl thioformate (CAS no. 59020-90-5), 5-methylfurfural (CAS no. 620-02-0), furfuryl acetate (CAS no. 623-17-6), 3-(2-furyl)acrolein (CAS no. 623-30-3), 2-thienylmercaptan (CAS no. 6258-63-5), 2,5-dimethylthiophene (CAS no. 638-02-8), 4-methyl-5-thiazolethanolacetate (CAS no. 656-53-1), 4-methylthiazole (CAS no. 693-95-8), 2-furyl-2-propanone (CAS no. 6975-60-6), 2-methyl-3-(2-furyl)prop-2-enal (CAS no. 874-66-8), 2-octylthiophene (CAS no. 880-36-4), ethyl 3-(furfurylthiol) propionate (CAS no. 94278-27-0), furfuryl alcohol (CAS no. 98-00-0), 3-acetyl-2,5-dimethylthiophene (CAS no. 2530-10-1), 2-acetylpyrrole (CAS no. 1072-83-9).

In a particularly preferred embodiment of the invention the at least one odor modulator compound of general formula (I) is selected from 2-ethyl-4-methylthiazole (CAS no. 15679-12-6), 2-isopropyl-4-methylthiazole (CAS no. 15679-13-7), 2-isobutylthiazole (CAS no. 18640-74-9), 2-acetylthiazole (CAS no. 24295-03-2), 2,2'-(dithiodimethylene)difuran (CAS no. 4437-20-1), furfuryl mercaptan (CAS no. 98-02-2), furfural propylene glycol acetal (CAS no. 4359-54-0), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), furaneol methyl ether (CAS no. 4077-47-8), sulfurol (CAS no. 13700-8), benzothiazole (CAS no. 95-16-9), 2-acetyl pyrrole (CAS no. 1072-83-9).

In a further preferred embodiment of the invention, the at least one odor modulator compound is an odor modulator compound of general formula (II),

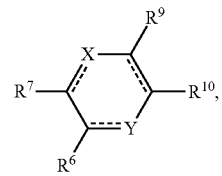

Formula (II)

where
X represents nitrogen or $CR^8$; and
Y represents nitrogen, $CR^{11}$ or $CR^{11}R^{12}$; and
$R^6$ and $R^8$ each represent, independently of one another, hydrogen or functional groups having 1 to 10 carbon atoms; and
$R^7$ and $R^9$ to $R^{12}$ each represent, independently of one another, hydrogen or functional groups having 1 to 4 carbon atoms,
where
the ring of formula (II) may contain, at the positions connected by dashed lines, each independently of one another, double bonds, with the proviso that the at least one odor modulator compound, if X or Y represents nitrogen, contains a double bond between X and the carbon atom of the ring of formula (II) that is linked to $R^7$, or between Y and the carbon atom of the ring of formula (II) that is linked to $R^6$, respectively; and
the carbon atoms of the ring of formula (II) that are linked to $R^6$ and $R^7$ may together be part of an annulated five-member or six-member ring, where functional groups $R^6$ and $R^7$ are each, independently of one another, an integral part of the annulated ring either completely or in part; and
one or more methyl groups, methylene groups, methine groups or quaternary carbon atoms of functional groups $R^6$ to $R^{12}$ may each, independently of one another, be substituted by heteroatoms; and
if Y represents $CR^{11}R^{12}$, there is no double bond between Y and the carbon atom of the ring that is connected to $R^6$.

Within the meaning of this embodiment, in the ring of general formula (II) the positions connected by dashed lines may each, independently of one another, comprise double bonds. However, double bonds are in particular not present if the natural valences of the atoms involved in the double bond are already saturated as a result of the selection of Y or functional groups $R^6$ to $R^{11}$. This means that the atoms involved in the double bond in principle have to be uncharged. If one of functional groups $R^6$ to $R^{11}$ forms a double bond to one of the carbon atoms in the ring of general formula (II), the corresponding atom in the ring can no longer be involved in a double bond within the ring.

The carbon atoms of the ring of formula (II) that are linked to $R^6$ and $R^7$ may together be part of an annulated five-member or six-member ring, where functional groups $R^6$ and $R^7$ are each, independently of one another, an integral part of the annulated ring either completely or in part. In this context, "annulated" means that two carbon rings share a carbon-to-carbon bond, specifically the carbon atoms of the ring of formula (II) that are linked to $R^6$ and $R^7$. If functional groups $R^6$ and $R^7$ are only in part an integral part of the annulated ring, the non-integral parts of the ring of the ring of functional groups $R^6$ and $R^7$ may, for example, be in the form of a side chain of the annulated ring.

The at least one odor modulator compound of general formula (II) preferably contains one to four heteroatoms, selected from the group of nitrogen, oxygen or sulfur.

Preferred functional groups $R^6$ to $R^{12}$ of general formula (II) are, for example, alkyl groups, alkenyl groups, aryl groups, hydroxy groups, alkanol groups, alkoxy groups, ether groups, acyl groups, (alkyl) ester groups, (alkyl) thiol groups, thioether groups and (alkyl) aldehyde groups. In principle, the various functional groups may be contained in functional groups $R^6$ to $R^{12}$ in any desired combination; however, within the meaning of the present invention, it is preferred, if $X=CR^8$ and $Y=CR^{11}$, for functional groups $R^6$ and $R^7$ to not be completely or in part an integral part of the five-member ring.

In a preferred embodiment of the invention, the at least one odor modulator compound of general formula (II) is selected from 2-acetylpyridine (CAS no. 1122-62-9), 2,5-dimethylpyrazine (CAS no. 123-32-0), 2,3,5-trimethylpyrazine (CAS no. 14667-55-1), 2-ethyl-3-methylpyrazine (CAS no. 15707-23-0), 2-acetylpyrazine (CAS no. 22047-25-2), 2-acetyl-3-methylpyrazine (CAS no. 23787-80-6), 2-isobutyl-3-methoxypyrazine (CAS no. 24683-00-9), 2,3-dimethylpyrazine (CAS no. 5910-89-4), 1-para-menthene-8-thiol (CAS no. 71159-90-5), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), 2-hydroxy-2-cyclohexen-1-one (CAS no. 10316-66-2), 2-(methylthio)phenol (CAS no. 1073-29-6), natural pyrazine mixture (CAS no. 84082-50-8), 2-methoxycinnamyl acetate (CAS no. 110823-66-0), 2,3,5,6-tetramethylpyrazine (CAS no. 1124-11-4), 2-hexylpyridine (CAS no. 1129-69-7), 2,6-dimethylthiophenol (CAS no. 118-72-9), 2-thiocresol (CAS no. 137-06-4), 2-ethylpyrazine (CAS no. 13925-00-3), 3-(2-methylpropyl)pyridine (CAS no. 14159-61-6), 2,3-diethylpyrazine (CAS no. 15707-24-1), 2-methyl-3-propylpyrazine (CAS no. 1598680-8), 2,3-dihydro-5,6-dimethylpyrazine (CAS no. 15986-92-2), 2,3-diethyl-5-methylpyrazine (CAS no. 18138-04-0), 2-(3-phenylpropyl)pyridine (CAS no. 2110-18-1), 2-pentylpyridine (CAS no. 2294-76-0), 5-methyl-6,7-dihydrocyclopentapyrazine (CAS no. 23747-48-0), 3-methylcyclohexane-1,2-dione (CAS no. 3008-43-3), 2-acetyl-3-ethylpyrazine (CAS no. 32974-92-8), 3-acetylpyridine (CAS no. 350-03-8), 2-pyrazineethanethiol (CAS no. 35250-53-4), 2-phenylethanethiol (CAS no. 4410-99-5), 2-ethylthiophenol (CAS no. 4500-58-7), 3-ethylpyridine (CAS no. 536-78-7), 2-ethyl-3(5/6)-dimethylpyrazine (CAS no. 55031-15-7), 3,5,5-trimethylcyclohexane-1,2-dione (CAS no. 57696-89-6), 1,2-cyclohexanediol (CAS no. 57794-08-8), 2-propylpyridine (CAS no. 622-39-9), 1-phenylethanethiol (CAS no. 6263-65-6), 2-isobutylpyridine (CAS no. 6304-24-1), 4-allyl-2,6-dimethoxyphenol (CAS no. 6627-88-9), 2-methylthio-3(5/6)methylpyrazine (CAS no. 67952-65-2), benzyl methyl disulfide (CAS no. 699-10-5), 2-methylquinoxaline (CAS no. 7251-61-8), 2-acetyl-3,5(6)-dimethylpyrazine (CAS no. 72797-17-2), ethyl 2-methoxybenzoate (CAS no. 7335-26-4), benzyl methyl sulfide (CAS no. 766-92-7), 2-methoxy-4-vinylphenol (CAS no. 7786-61-0), para-mentha-8-thioacetat-3-one (CAS no. 9429357-9), maltol (CAS no. 118-71-8).

In a particularly preferred embodiment of the invention, the at least one odor modulator compound of general formula (II) is selected from 2-acetylpyridine (CAS no. 1122-62-9), 2,5-dimethylpyrazine (CAS no. 123-32-0), 2,3,5-trimethylpyrazine (CAS no. 14667-55-1), 2-ethyl-3-methylpyrazine (CAS no. 15707-23-0), 2-acetylpyrazine (CAS no. 22047-25-2), 2-acetyl-3-methylpyrazine (CAS no. 23787-80-6), 2-isobutyl-3-methoxypyrazine (CAS no. 24683-00-9), 2,3-dimethylpyrazine (CAS no. 5910-89-4), 1-para-menthene-8-thiol (CAS no. 71159-90-5), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 3846222-5), thiocineol (CAS no. 68398-18-5), maltol (CAS no. 118-71-8).

In a further preferred embodiment of the invention, the at least one odor modulator compound is an odor modulator compound of general formula (III),

Formula (III)

where
  X represents $CHR^{14}$, sulfur or a carbonyl group; and
  Y represents $CHR^{16}$, sulfur, $CR^{16}R^{17}$ or a carbonyl group; and
  $R^{13}$, $R^{14}$ and $R^{17}$ each represent, independently of one another, hydrogen or functional groups having 1 to 4 carbon atoms; and
  $R^{15}$ and $R^{16}$ each represent, independently of one another, hydrogen or functional groups having 1 to 8 carbon atoms,
where
  functional groups $R^{13}$ to $R^{17}$ are open-chain; and
  one or more methyl groups, methylene groups, methine groups or quaternary carbon atoms of functional groups $R^{13}$ to $R^{17}$ may each, independently of one another, be substituted by heteroatoms.

In a preferred embodiment of the invention, the at least one odor modulator compound is of general formula (III), where
  X represents $CHR^{14}$, sulfur or a carbonyl group; and
  Y represents $CHR^{16}$, sulfur or a carbonyl group; and
  $R^{13}$ and $R^{14}$ each represent, independently of one another, hydrogen or functional groups having 1 to 3 carbon atoms; and
  $R^5$ and $R^{16}$ each represent, independently of one another, hydrogen or functional groups having 1 to 7 carbon atoms,
where
  functional groups $R^{13}$ to $R^{16}$ are open-chain; and
  one or more methyl groups, methylene groups, methine groups or quaternary carbon atoms of functional groups $R^{13}$ to $R^{16}$ may each, independently of one another, be substituted by heteroatoms.

Functional groups $R^{13}$ to $R^{17}$ of the at least one odor modulator compound of general formula (III) are open-chain. Within the meaning of the present invention, "open-chain" means that none of functional groups $R^{13}$ to $R^{17}$ as such forms a ring or is involved in a ring and that no rings are formed between individual functional groups $R^{13}$ to $R^{17}$ either. However, "open-chain" in particular does not mean that functional groups $R^{13}$ to $R^{17}$ could not comprise double or triple bonds between two directly neighboring atoms.

The at least one odor modulator compound of general formula (III) preferably contains one to four heteroatoms, selected from the group of nitrogen, oxygen or sulfur.

In a preferred embodiment of the invention, the at least one odor modulator compound of general formula (III) is selected from ethyl 3-methylthiopropionate (CAS no. 13327-56-5), methyl 3-methylthiopropionate (CAS no. 13532-18-8), 4-methylthio-4-methylpentan-2-one (CAS no. 23550-40-5), S-methyl butanethioate (CAS no. 2432-51-1), 3-methylthio-1-hexanol (CAS no. 51755-66-9), dibutyl sulfide (CAS no. 544-40-1), dipropyl sulfide (CAS no. 111-47-7), 1-(methylthio)-2-butanone (CAS no. 13678-58-5), 3-acetylthiohexylacetate (CAS no. 136954-25-1), 1-methylthio-2-propanone (CAS no. 14109-72-9), S-methyl thioacetate (CAS no. 1534-08-3), bis-(methylthio)methane (CAS no. 1618-26-4), 3-methylthiobutanal (CAS no. 16630-52-7), 3-(methylthio)propylacetate (CAS no. 16630-55-0), 3-(methylthio)propylbutyrate (CAS no. 1663060-7), methyl (methylthio)acetate (CAS no. 16630-66-3), ethyl methyl disulfide (CAS no. 20333-39-5), diallyl trisulfide (CAS no. 2050-87-5), 4-methylthiobutanol (CAS no. 20582-85-8), diallyl disulfide (CAS no. 2179-57-9), allyl methyl sulfide (CAS no. 2179-58-0), Allyl propyl disulfide (CAS no. 217959-1), 2,3-dithiahexane (CAS no. 2179-60-4), 2-methylthioacetaldehyde (CAS no. 23328-62-3), ethyl propyl disulfide (CAS no. 30453-31-7), 3-methylthiopropanal (CAS no. 3268-49-3), 4-(methylthio)-2-butanone (CAS no. 34047-39-7), 3-methylthiohexanal (CAS no. 38433-74-8), 3-methylthiopropylamine (CAS no. 4104-45-4), S-Methyl-2-methylbutanethioate (CAS no. 42075-45-6), diisopropyl disulfide (CAS no. 4253-89-8), ethyl 2-(methylthio)acetate (CAS no. 4455-13-4), ethyl 2-methyl-2-methylthiopropionate (CAS no. 49773-24-2), 2-(ethylthio)-1-propanol (CAS no. 72311-96-7), 3-methylthiopropanol (CAS no. 505-10-2), 3-methylthiopropylisothiocyanate (CAS no. 505-79-3), methyl 2-(methylthio)butyrate (CAS no. 51534-66-8), 3-methylthio-hex-1-ylacetate (CAS no. 5175585-2), 2-(methylthio)ethanol (CAS no. 5271-38-5), methyl 4-methylthiobutyrate (CAS no. 53053-51-3), dipropyl trisulfide (CAS no. 6028-61-1), S-methyl-4-methyl pentanethioate (CAS no. 61122-71-2), dimethyl disulfide (CAS no. 624-92-0), ethyl thioacetate (CAS no. 625-60-5), n-butyl methyl sulfide (CAS no. 628-29-5), dipropyl disulfide (CAS no. 629-19-6), 2,4,6-trithiaheptane (CAS no. 6540-86-9), amyl methyl disulfide (CAS no. 72437-68-4), methyl thiomethyl hexanoate (CAS no. 74758-91-1), methyl thiomethyl butyrate (CAS no. 74758-93-3), isoamyl-3-methylthiopropionate (CAS no. 93762-35-7), 1-(methylthio)pentan-3-one (CAS no. 66735-69-1), 3-(methylthio)propylmercaptoacetate (CAS no. 852997-30-9), methyl isobutanethioate (CAS no. 42075-42-3).

In a particularly preferred embodiment of the invention, the at least one odor modulator compound of general formula (III) is selected from ethyl 3-methylthiopropionate (CAS no. 13327-56-5), methyl 3-methylthiopropionate (CAS no. 13532-18-8), 4-methylthio-4-methylpentan-2-one (CAS no. 23550-40-5), S-methyl butanethioate (CAS no. 2432-51-1), 3-methylthio-1-hexanol (CAS no. 51755-66-9), dibutyl sulfide (CAS no. 544-40-1), 1-(methylthio)pentan-3-one (CAS no. 66735-69-1), 3-(methylthio)propylmercaptoacetate (CAS no. 852997-30-9), methyl isobutanthioate (CAS no. 42075-42-3).

In a further preferred embodiment of the invention, the at least one odor modulator compound is an odor modulator compound of general formula (IV),

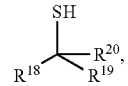

Formula (IV)

where
$R^{18}$ and $R^{19}$ each represent, independently of one another, hydrogen or a functional group having 1 to 3 carbon atoms; and
$R^{20}$ represents a functional group having 3 to 10 carbon atoms,
where
functional groups $R^{18}$ to $R^{20}$ are open-chain; and
one or more methyl groups, methylene groups, methine groups or quaternary carbon atoms of functional groups $R^{18}$ to $R^{20}$ may each, independently of one another, be substituted by heteroatoms,
with the proviso that the at least one odor modulator compound of general formula (IV) is not 3-mercapto-1-hexenol (CAS no. unknown), 3-mercapto-3-methyl-1-hexanol (CAS no. 307964-23-4), 3-mercapto-2-methylbutan-1-ol (CAS no. 227456-33-9), 3-mercaptopentan-1-ol (CAS no. 548740-99-4) or 3-mercaptohexan-1-ol (CAS no. 51755-83-0).

In a preferred embodiment of the invention, the at least one odor modulator compound is of general formula (IV), where
$R^{18}$ and $R^{19}$ each represent, independently of one another, hydrogen or a methyl group,
where it is preferred for $R^{18}$ to represent a methyl group and $R^{19}$ to represent hydrogen; and
$R^{20}$ represents a functional group having 3 to 10 carbon atoms, preferably a functional group having 3 to 8 carbon atoms,
where
at least one methyl group, methylene group, methine group or quaternary carbon atom of functional group $R^{20}$ is substituted by a heteroatom, preferably oxygen.

Functional groups $R^{18}$ to $R^{20}$ of the at least one odor modulator compound of general formula (IV) are open-chain. Within the meaning of the present invention, "open-chain" means that none of functional groups $R^{18}$ to $R^{20}$ as such forms a ring or is involved in a ring and that no rings are formed between individual functional groups $R^{18}$ to $R^{20}$ either. However, "open-chain" in particular does not mean that functional groups $R^{18}$ to $R^{20}$ could not comprise double or triple bonds between two directly neighboring atoms.

The odor modulator compound of general formula (IV) preferably contains one to four additional heteroatoms, selected from the group of nitrogen, oxygen or sulfur, in particular oxygen being preferred.

One or more methyl groups, methylene groups, methine groups or quaternary carbon atoms of functional groups $R^1$ to $R^{20}$ of the at least one odor modulator compound according to one the above-mentioned preferred embodiments may each, independently of one another, be substituted by heteroatoms. Heteroatoms within the meaning of the present invention are selected from the group of nitrogen, oxygen, sulfur, silicon, selenium, fluorine, chlorine, bromine or iodine. One or more methyl groups may be substituted by a heteroatom selected from the group of nitrogen, oxygen, sulfur, silicon, selenium, fluorine, chlorine, bromine or iodine, one or more methylene groups may be substituted by a heteroatom selected from the group of nitrogen, oxygen, sulfur, selenium or silicon, one or more methine groups may be substituted by a heteroatom selected from the group of nitrogen or silicon, and one or more quaternary carbon atoms may be substituted by silicon. If one or more methyl groups, methylene groups, methine groups or quaternary carbon atoms of functional groups $R^1$ to $R^{20}$ is substituted by heteroatoms, this means that the corresponding group is exchanged for a heteroatom. If free valences arise as a result of the substitution of a methyl group, a methylene group or a methine group, these are in principle saturated with hydrogen. A terminal methyl group adjacent to a methylene group may therefore, for example, be exchanged for a hydroxy group or a sulfanyl group such that a methylene hydroxy group or methylene thiol group is obtained. Similarly, an isopropyl group that is a functional group having two methyl groups and a methine group, or a derivative of the isopropyl group that is a functional group having a methyl group, a methylene group and a quaternary carbon atom, may have the following substitution model, for example:

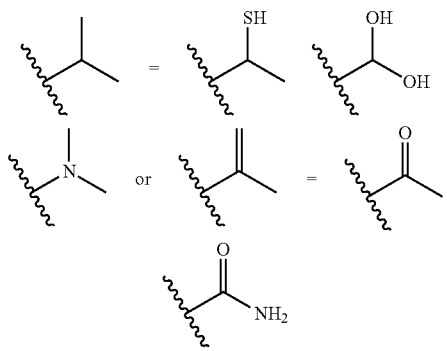

Methyl groups, methylene groups, methine groups or quaternary carbon atoms of functional groups $R^1$ to $R^{20}$ may in principle be substituted as desired by heteroatoms; however, with the exception of disulfides or polysulfides and diazo compounds, no two directly neighboring groups are both substituted by heteroatoms.

In a preferred embodiment of the invention, the composition according to the invention contains one to six odor modulator compounds, preferably one to five odor modulator compounds, more preferably one to four odor modulator compounds, and most preferably one to three odor modulator compounds.

Within the meaning of this invention, the expression "the composition contains at least one odor modulator compound" means that the at least one odor modulator compound is a component of the microcapsules according to the invention, for example in the core of a core/shell capsule. A composition according to the invention may, however, additionally contain further non-encapsulated odor modulator compounds.

In a further preferred embodiment of the invention, the at least one odor modulator compound, based on the total of all the odorants contained in the composition according to the invention, is used in a weight ratio of at most 1:9, preferably at most 1:49, more preferably at most 1:99, and most preferably at most 1:299, the ratio always being based on the at least one odorant as such and not on a corresponding odorant precursor compound.

In a further preferred embodiment of the invention, the at least one odor modulator compound is contained in the composition according to the invention in an amount of from 2 wt. % to 0.000001 wt. %, preferably from 1.5 wt. % to 0.000001 wt. %, more preferably from 1.0 wt. % to 0.000001 wt. %, even more preferably from 0.5 wt. % to 0.000001 wt. %, most preferably from 0.25 wt. % to 0.000001 wt. %, with wt. % based in each case on the total of all the odorants contained in the composition.

On account of the low ratio of the at least one odor modulator compound in comparison with the odorants contained in the composition according to the invention, and the low amounts of the individual odor modulator compounds, it is ensured that the fragrance profile of the composition is changed negligibly at best, such that a person skilled in the art still recognizes the fragrance profile of the original fragrance. Furthermore, from an ecological and economical perspective, it is advantageous to use only small amounts of the odor modulator compound.

In a preferred embodiment of the invention, the at least one odor modulator compound contains one to five heteroatoms, preferably one to four heteroatoms, and most preferably one to three heteroatoms, selected from the group of N, O or S.

In a preferred embodiment of the invention, the at least one odor modulator compound has a molecular weight of lower than 250 g mol$^{-1}$, preferably lower than 225 g mol$^{-1}$, and more preferably lower than 200 g mol$^{-1}$.

In another preferred embodiment of the invention, the at least one odor modulator compound has a boiling point of lower than 250° C., preferably lower than 225° C., more preferably 200° C., and most preferably lower than 175° C.

In yet a further preferred embodiment of the invention, an efficiency factor according to the formula according to the invention $$E = \frac{P_{GMV}}{P+1} \geq 1.15$$

of at least 1.5, preferably at least 1.75, and most preferably at least 2.0 is achieved on account of the at least one odor modulator compound.

In another preferred embodiment of the invention, the at least one odor modulator compound has an odor detection threshold of lower than 100 ppb, preferably lower than 75 ppb, more preferably lower than 50 ppb, even more preferably lower than 35 ppb, even more preferably lower than 10 ppb, most preferably lower than 1 ppb.

The at least one odor modulator compound is preferably characterized by a lower odor detection threshold (ODT). The odor detection threshold is the lowest concentration of a substance that can still be smelled. A simple technique for determining the odor detection threshold is dynamic olfactometry, during which a direct sensory assessment of the compounds takes place. The odor detection threshold is used as a measure for the strength of the odor of a fragrance. The odor detection threshold (ODT) of the at least one odor modulator compound is determined according to DIN EN 13725:2003 and is preferably lower than 100 ppb, more preferably lower than 75 ppb, even more preferably lower than 50 ppb, even more preferably lower than 35 ppb, even more preferably lower than 10 ppb, and most preferably lower than 1 ppb. Detailed information can be read, for example, from DIN EN 13725:2003. For the purpose of the present invention, the odor detection threshold is measured according to the following method:

The olfactometer is located in a chamber (measuring chamber) specifically designed for the olfactometer, which chamber is odorless, can be well ventilated and can optionally be subject to forced ventilation by means of an activated carbon filter. The volume fraction of carbon dioxide in the measuring chamber is less than 0.15 vol. %; the air exchange rate is at least 4.4 m³/h per person. The temperature in the measuring chamber is 22±3° C. and is constant during the measurement. The measuring chamber is not exposed to any direct solar radiation, and other interfering sources of light and noise are also minimized as far as possible. The olfactometer and all devices which come into direct or indirect contact with the odor modulator compound to be assessed have to be odorless, and are inert in relation to their reactivity with the odor modulator compounds, such as glass, stainless steel or PTFE. The air flow provided by the olfactometer has to be at least 20 l/min, the opening in the device at which the sensory assessment is carried out being formed such that the air speed in the throughflow opening is at least 0.2 m/s. The olfactometer is checked regularly, or upon at least every twelfth compound, by means of a reference measurement, with n-butanol as the reference compound. The compounds are assessed by at least four testers, with generally equal numbers of men and women trained in odors being employed, all of whom are at least 16 years old.

At the time the compounds are assessed, the testers are not influenced by interfering factors such as contact with perfumes, food, other natural stimulants or by colds or allergies. From the odor modulator compound, standardized diluted solutions are produced in an odorless solvent, for example dipropylene glycol (DPG), the smallest concentration being considerably below the odor threshold. Subsequently, the solutions are measured by means of the olfactometer. The concentration of the compound to be assessed is increased incrementally, the concentration being doubled each time until the tester perceives an odor. Each odor modulator compound is measured three times by each tester, and the arithmetic mean of all concentrations at which an odor was perceived forms the odor detection threshold (ODT).

In a further preferred embodiment of the invention, the at least one odor modulator compound is selected from pyrroles, pyridines, pyrazines, thiols, sulfides, thiazoles, thiophenes, furans, oxazolines, oxazoles and/or oxathiones.

At least one odor modulator compound is contained in the microcapsules of feature a). In a preferred embodiment of the invention, the microcapsules are core/shell microcapsules, core/shell microcapsules being, within the meaning of the present invention, capsules that comprise, as an outer shell, a wall material that is preferably solid at room temperature. The capsule core contains the at least one odor modulator compound according to the invention and preferably at least one odorant. According to the invention, the core may be liquid or gel-like. In this case it is possible for the at least one odor modulator compound to be contained in the core of the capsule substantially as a pure substance. Alternatively, capsules are also conceivable in which the capsule core comprises, in addition to the at least one odor modulator compound, further ingredients, such as solvents, stabilizers or the at least one odorant.

DETAILED DESCRIPTION OF THE INVENTION

It has been demonstrated that it is advantageous to encapsulate the at least one odor modulator compound since the at least one odor modulator compound generally has a relatively low boiling point and at the same time a high vapor pressure, meaning that the at least one odor modulator compound volatilizes relatively quickly. By using at least one encapsulated odor modulator compound, the advantageous effect of the at least one odor modulator compound can be provided even over a longer period of time.

The composition according to the invention contains the microcapsules preferably in an amount of from 0.0005 to 0.15 wt. %, particularly preferably from 0.001 to 0.1 wt. %, very particularly preferably from 0.01 to 0.1 wt. %.

The capsules that can be used according to the invention are preferably water-insoluble capsules. The water-insolubility of the capsules has the advantage that said capsules are thus able to outlast the washing or cleaning process and are thus capable of releasing the at least one odor modulator compound and preferably the at least one odorant only after the water-based washing or cleaning process, for example during drying as a result of an increase in temperature or e.g. as a result of exposure to sunlight when clothing is worn or when the surface is subject to friction.

In a preferred embodiment of the invention, the microcapsules have a semipermeable capsule wall (shell), and the core of the capsule comprises at least 50 wt. % of the at least one odor modulator compound, capsules of this kind being preferably free of odorants.

A semipermeable capsule wall within the meaning of the present invention is a capsule wall that is semipermeable, i.e. continuously releases small amounts of the capsule core over time without the capsule having been e.g. damaged or opened by friction. Capsules of which the core contains at least 50 wt. % of the at least one odor modulator compound continuously released small amounts of the at least one odor modulator compound over a longer period of time, resulting in an initial and long-lasting increase in the fragrance intensity.

In a further preferred embodiment of the invention, the microcapsules have an impermeable shell, and the capsule core comprises, in addition to the at least one odor modulator compound, at least 70 wt. %, preferably at least 80 wt. %, and most preferably at least 85 wt. %, of the at least one odorant.

An impermeable shell within the meaning of the present invention is a capsule wall that is substantially impermeable, i.e. only releases the capsule core when the capsule is damaged or opened. Capsules of this kind contain significant amounts of the at least one odorant in the capsule core, and therefore, when the capsule is damaged or opened, a very intense fragrance is provided. The fragrance intensities thus achieved are generally so high that smaller amount of the microcapsules can be used to achieve the same fragrance intensity as in the case of conventional microcapsules.

In a preferred embodiment of the invention, the composition according to the invention, in particular a textile treatment agent according to the invention, contains both microcapsules having a semipermeable shell and microcapsules having an impermeable shell. By using the two types of capsules, a considerably improved fragrance intensity can be provided over the course of the entire washing cycle.

In a further preferred embodiment of the invention, the composition according to the invention may also contain two or more different microcapsule types having a semipermeable or impermeable shell.

Possible materials for the shell of the capsules are typically high-molecular compounds, such as protein compounds (for example, gelatine, albumin, casein and others), cellulose derivatives (for example, methyl cellulose, ethyl cellulose, cellulose acetate, cellulose nitrate, carboxymethyl cellulose and others) and especially also synthetic polymers (for example polyamides, polyethylene glycols, polyurethanes, epoxy resins and others). Melamine/formaldehyde polymer, melamine/urea polymer, melamine/urea/formaldehyde polymer, polyacrylate polymer or polyacrylate copolymer is preferably used as the wall material, i.e. the shell. Capsules according to the invention are, for example, though not exclusively, described in US 2003/0125222 A1, DE 10 2008 051 799 A1 or WO 01/49817.

Preferred melamine/formaldehyde microcapsules are produced by condensing melamine/formaldehyde precondensates and/or $C_1$-$C_4$ alkyl ethers thereof in water in which the at least one odor modulator compound and optionally further ingredients, e.g. at least one odorant, in the presence of a protective colloid. Suitable protective colloids are e.g. cellulose derivatives, such as hydroxyethyl cellulose, carboxymethyl cellulose and methyl cellulose, polyvinyl pyrrolidone, copolymers of N-vinylpyrrolidone, polyvinyl alcohols, partially hydrolyzed polyvinyl acetates, gelatine, gum arabic, xanthan gum, alginates, pectins, degraded starches, casein, polyacrylic acid, polymethacrylic acid, copolymers of acrylic acid and methacrylic acid, water-soluble polymers, comprising sulfonic acid groups, that have a content of sulfoethyl acrylate, sulfoethyl methacrylate or sulfopropyl methacrylate, and polymers of N-(sulfoethyl)-maleinimide, 2-acrylamido-2-alkylsulfonic acids, styrene sulfonic acids and formaldehyde, and condensates of phenol sulfonic acids and formaldehyde.

It is preferred to coat the microcapsules used according to the invention, over part of or the whole surface thereof, with at least one cationic polymer. Accordingly, a suitable cationic polymer for coating the microcapsules is at least one cationic polymer from polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-43, polyquaternium-44, polyquaternium-45, polyquaternium-46, polyquaternium-47, polyquaternium-48, polyquaternium-49, polyquaternium-50, polyquaternium-51, polyquaternium-56, polyquaternium-57, polyquaternium-61, polyquaternium-69, polyquaternium-86. Polyquaternium-7 is very particularly preferred. The polyquaternium nomenclature of the cationic polymers that is used within the scope of this application is taken from the declaration of cationic polymers according to the International Nomenclature of Cosmetic Ingredients (INCI declaration).

Capsules that can be used preferably have an average diameter $X_{50.3}$ in the range of from 1 to 100 μm, preferably from 5 to 95 μm, in particular from 10 to 90 μm, for example from 10 to 80 μm.

The shell of the capsules that surrounds the core or (filled) cavity preferably has an average thickness in the range of from around 5 to 500 nm, preferably from around 50 to 200 nm, in particular from around 70 nm to approximately 180 nm.

The liquid composition according to the invention preferably contains water. In this case it is preferred for the composition according to the invention to contain more than 5 wt. %, preferably more than 15 wt. %, and particularly preferably more than 25 wt. %, water.

In addition, non-aqueous solvents may be added to the compositions according to the invention. Suitable non-aqueous solvents include monovalent or polyvalent alcohols, alkanol amines or glycol ethers, provided that they are water-miscible in the specified concentration range. The solvents are preferably selected from ethanol, n-propanol, i-propanol, butanols, glycol, propanediol, butanediol, methyl propanediol, glycerol, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether and mixtures of these solvents. However, it is preferred for the composition according to the invention to contain an alcohol, in particular ethanol and/or glycerol, in amounts of between 0.5 and 5 wt. %.

In a preferred embodiment of the invention, the composition according to the invention contains at least one surfactant selected from anionic, cationic or nonionic surfactants.

If the liquid composition according to the invention is formed as a washing or cleaning agent, in particular as a transparent washing agent for textiles, sulfonates and/or sulfates are preferably used as an anionic surfactant. The preferred total amount of anionic surfactant in the washing or cleaning agent, in particular in a transparent liquid washing agent for textiles, is from 7.5 to 65.0 wt. % and preferably from 20.0 to 45 wt. %, in each case based on the overall agent.

Suitable sulfonate-type surfactants are preferably $C_{9-13}$ alkyl benzene sulfonates, olefin sulfonates, i.e. mixtures of alkene and hydroxyalkane sulfonates, and disulfonates, as are obtained, for example, from $C_{12-18}$ monoolefins having a terminal or internal double bond by way of sulfonation with gaseous sulfur trioxide and subsequent alkaline or acid hydrolysis of the sulfonation products. $C_{12-18}$ alkane sulfonates and esters of alpha-sulfo fatty acids (ester sulfonates), for example alpha-sulfonated methyl esters of hydrogenated coconut, palm kernel or tallow fatty acids, are also suitable. $C_{9-13}$ alkyl benzene sulfonates are particularly preferred.

Alkali salts, and in particular sodium salts, of sulfuric acid semiesters of $C_{12}$-$C_{18}$ fatty alcohols, for example from coconut fatty alcohol, tallow fatty alcohol, lauryl alcohol, myristyl alcohol, cetyl alcohol or stearyl alcohol, or of $C_{10}$-$C_{20}$ oxo-alcohols and semiesters of secondary alcohols having these chain lengths are preferred as alk(en)yl sulfates. In the interest of washing, $C_{12}$-$C_{16}$ alkyl sulfates, $C_{12}$-$C_{15}$ alkyl sulfates and $C_{14}$-$C_{15}$ alkyl sulfates are preferred. 2,3-alkyl sulfates are also suitable anionic surfactants.

Fatty alcohol ether sulfates, such as sulfuric acid monoesters of straight-chain or branched $C_{7-21}$ alcohols ethoxylated having 1 to 6 moles of ethylene oxide, such as 2-methyl-branched $C_{9-11}$ alcohols having, on average, 3.5 moles of ethylene oxide (EO) or $C_{12-18}$ fatty alcohols having 1 to 4 EO, are particularly suitable sulfate-type surfactants according to the invention.

Further suitable anionic surfactants are soaps. Saturated and unsaturated fatty acid soaps are suitable, such as salts of lauric acid, myristic acid, palmitic acid, stearic acid, (hydrogenated) erucic acid and behenic acid, and in particular soap mixtures derived from natural fatty acids, such as coconut, palm kernel, olive oil or tallow fatty acids.

The anionic surfactants and the soaps may be in the form of sodium, potassium, magnesium or ammonium salts thereof. The anionic surfactants are preferably in the form of ammonium salts thereof. Preferred counterions for the anionic surfactants are protonated forms of choline, triethyl amine, monoethanolamine or methyl ethyl amine.

Cationic surfactants are preferably used in textile treatment compositions according to the invention that are intended to make the textile soft. Cationic surfactants are preferably selected from among esterquats and/or quaternary ammonium compounds (QAC) of general formula $(R^I)(R^{II})(R^{III})(R^{IV})N^+X^-$, in which $R^I$ to $R^{IV}$ represent $C_{1-22}$ alkyl functional groups, $C_{7-28}$ arylalkyl functional groups or heterocyclic functional groups that are the same or different, wherein two functional groups or, in the case of aromatic bonding such as in pyridine, even three functional groups form, together with the nitrogen atom, the heterocycle, e.g. a pyridinium or imidazolinium compound, and $X^-$ represents halide ions, sulfate ions, hydroxide ions or similar anions. QACs can be produced by reacting tertiary amines with alkalizing agents, e.g. methyl chloride, benzyl chloride, dimethyl sulfate, dodecyl bromide or also ethylene oxide. The alkylation of tertiary amines with a long alkyl functional group and two methyl groups is particularly simple; the quaternization of tertiary amines with two long functional groups and a methyl group can also be carried out under mild conditions using methyl chloride. Amines having three long alkyl functional groups or hydroxy-substituted alkyl functional groups are less reactive, and are quaternized e.g. using dimethyl sulfate. Examples of suitable QACs are benzalkonium chloride (N-alkyl-N,N-dimethylbenzylammonium chloride), Benzalkon B (m,p-dichlorobenzyldimethyl-$C_{12}$-alkylammonium chloride, benzoxonium chloride (benzyldodecyl-bis-(2-hydroxyethyl) ammonium chloride), cetrimonium bromide (N-hexadecyl-N,N-trimethylammonium bromide), benzethonium chloride (N,N-dimethyl-N-\[2-\[2-\[p-(1,1,3,3-tetramethylbutyl)phenoxy]ethoxy]ethyl] benzylammonium chloride), dialkyldimethylammonium chlorides such as di-n-decyldimethylammonium chloride, didecyldimethylammonium bromide, dioctyldimethylammonium chloride, 1-cetylpyridinium chloride and thiazolinium iodide, and mixtures thereof. Preferred QACs are benzalkonium chlorides having $C_8$-$C_{22}$ alkyl functional groups, in particular $C_{12}$-$C_{14}$ alkylbenzyldimethylammonium chloride.

In order to prepare transparent, liquid compositions, at least one cationic surfactant is particularly suitable, which can be obtained by reacting
(i) a mixture of at least one dicarboxylic acid of formula (K-I)

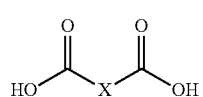

(K-I)

where X represents a saturated or unsaturated hydrocarbon functional group having 1 to 8 carbon atoms, and of at least one monocarboxylic acid of formula (K-II)

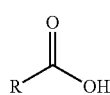

(K-II)

where R represents a saturated or unsaturated hydrocarbon functional group having 5 to 21 carbon atoms, with
(ii) at least one tertiary amine of formula (K-III)

(K-III)

where R', R" and R'" represent, independently of one another, a ($C_2$ to $C_6$) hydroxyalkyl group, in particular 2-hydroxyethyl,
and by subsequently reacting the resulting product with
(iii) at least one quaternization agent for quaternizing at least one amino group contained in the reaction product.

For example, dicarboxylic acids that are in principle suitable as ingredients within the meaning of the invention, include those of formula (K-I) in which X represents an optionally hydroxy-substituted, straight-chain or branched alkylene group having 1 to 8 carbon atoms. While not limiting, typical examples are succinic acid, maleic acid, glutaric acid, and in particular adipic acid. X preferably represents ethane-1,2-diyl, propane-1,2-diyl, propane-1,3-diyl, butane-1,4-diyl, hexane-1,4-diyl or cyclohexane-1,4-diyl, particularly preferably butane-1,4-diyl. The dicarboxylic acid of formula (K-I) is preferably adipic acid.

In the monocarboxylic acids of formula (K-II), RCO preferably represents an aliphatic, linear or branched acyl functional group having 6 to 22 carbon atoms and 0 and/or 1, 2 or 3 double bonds. Typical examples include, with being limited hereto, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid and erucic acid, and technical mixtures thereof, which accumulate e.g. during the pressurized splitting of natural fats and oils, or during the reduction of aldehydes from Roelen oxosynthesis or the dimerization of unsaturated fatty acids. Stearic acid, isostearic acid, palmitic acid, myristic acid, lauric acid, capric acid, caprylic acid, 2-ethylhexanoic acid, 2-octyldodecanoic acid, caproic acid, oleic acid, linoleic acid, linolenic acid, partially hardened coconut fatty acid, palm fatty acid, palm kernel fatty acid, tallow fatty acid and mixtures of two or more of the above-mentioned acids are preferred.

Generally, R particularly preferably represents, in formula (K-II), a linear or branched $C_5$ to $C_{21}$ hydrocarbon functional group having 0 to 3 double bonds. The monocarboxylic acid of formula (K-II) is preferably stearic acid.

Alkanol amines of formula (K-III) that are suitable as central nitrogen compounds within the meaning of the invention contain a hydroxyalkane functional group (alkanol functional group) having 2 to 6 carbon atoms, preferably 2 to 4 carbon atoms. Triethanolamine is preferably used.

In a particularly preferred embodiment, the at least one cationic surfactant comprises at least one compound of formula (K1)

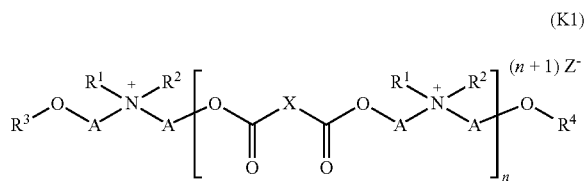

(K1)

or consists thereof.

X represents a saturated or unsaturated hydrocarbon functional group having 1 to 10 carbon atoms, in particular butane-1,4-diyl, A represents a ($C_2$ to $C_6$) alkane diyl group, in particular ethane-1,2-diyl, $R^1$ represents a ($C_2$ to $C_4$) hydroxyalkyl group or a ($C_6$ to $C_{22}$) acyloxy ($C_2$ to $C_4$) alkyl group, in particular 2-hydroxyethyl or 2-(($C_6$ to $C_{22}$)acyloxy)ethyl, R represents methyl or ethyl, $R^3$ and $R^4$ represent, independently of one another, a hydrogen atom or a ($C_6$ to $C_{22}$) acyl group, n represents 1 or 2, and $Z^-$ represents any desired anion, in particular methyl sulfate, with the proviso that, according to formula (K1), at least one of groups $R^1$, $R^3$ or $R^4$ comprises a ($C_6$ to $C_{22}$) acyl functional group.

Cationic surfactants, if contained, are preferably contained in amounts of preferably from 5 wt. % to 50 wt. %, in particular from 8 wt. % to 30 wt. %.

Suitable nonionic surfactants include alkoxylated fatty alcohols, alkoxylated fatty acid alkyl esters, fatty acid amides, alkoxylated fatty acid amides, polyhydroxy fatty acid amides, alkyl phenol polyglycol ethers, amine oxides, alkyl polyglucosides and mixtures thereof.

Nonionic surfactants that are preferably used are alkoxylated, advantageously ethoxylated, in particular primary alcohols having preferably 8 to 18 C atoms and, on average, 4 to 12 moles of ethylene oxide (EO) per mole of alcohol, in which alcohols the alcohol functional group may be linear or preferably methyl-branched in the 2 position or may contain linear and methyl-branched functional groups in mixture, as are usually present in oxo-alcohol functional groups. However, alcohol ethoxylates, having linear functional groups, of alcohols of native origin having 12 to 18 C atoms, for example of coconut, palm, tallow fatty or oleyl alcohol, and an average of 5 to 8 EO per mole of alcohol are particularly preferred. Examples of preferred ethoxylated alcohols are $C_{12-14}$ alcohols having 4 EO or 7 EO, $C_{9-11}$ alcohols having 7 EO, $C_{13-15}$ alcohols having 5 EO, 7 EO, 7 EO or 8 EO, $C_{12-18}$ alcohols having 5 EO or 7 EO, and mixtures thereof. The degrees of ethoxylation indicated are statistical averages which, for a specific product, may be an integer or a fraction. Preferred alcohol ethoxylates have a narrowed homolog distribution (narrow range ethoxylates, NRE). In addition to these nonionic surfactants, fatty alcohols having more than 12 EO may also be used. Examples of these are tallow fatty alcohols having 14 EO, 25 EO, 30 EO or 40 EO. Non-ionic surfactants comprising EO and PO groups together in the molecule can be used according to the invention. Furthermore, a mixture of a (more highly) branched ethoxylated fatty alcohol and an unbranched ethoxylated fatty alcohol, such as a mixture of a $C_{16-18}$ fatty alcohol having 7 EO and 2-propylheptanol having 7 EO, is also suitable. The agent according to the invention particularly preferably contains a $C_{12-18}$ fatty alcohol having 7 EO, a $C_{13-15}$ oxo-alcohol having 7 EO and/or a $C_{13-15}$ oxo-alcohol having 8 EO as a nonionic surfactant.

The total amount of nonionic surfactant in a composition according to the invention, if comprising nonionic surfactant, is preferably from 0.1 to 25 wt. % and preferably from 7 to 22 wt. %, in each case based on the overall agent.

The composition according to the invention may additionally contain further ingredients that further improve the application-specific and/or aesthetic properties of the composition depending on the intended application. Within the scope of the present invention, the compositions according to the invention, in particular if they are suitable as textile treatment agents (e.g. as a washing agent or softener), may contain builders, bleaching agents, bleach activators, bleach catalysts, esterquats, silicone oils, emulsifiers, thickeners, electrolytes, pH adjusters, fluorescing agents, dyes, hydrotropes, suds suppressors, anti-redeposition agents, solvents, enzymes, optical brighteners, graying inhibitors, anti-shrink agents, anti-crease agents, dye transfer inhibitors, color protectants, wetting agents, antimicrobial active ingredients, germicides, fungicides, antioxidants, corrosion inhibitors, preservatives, antistatic agents, ironing aids, repellent and impregnation agents, polymers, anti-swell and anti-slip agents, and UV absorbers.

The amounts of the individual ingredients in the compositions according to the invention depend on the intended purpose of the agents in question, and a person skilled in the art is in principle familiar with the ranges of the amounts of ingredients that should be used, or may obtain these from the relevant technical literature. Depending on the intended purpose of the compositions according to the invention, for example as a textile treatment or cleaning agent, the surfactant content is selected to be higher or lower.

A composition according to the invention suitable as a textile or cleaning agent preferably contains at least one water-soluble, organic and/or water-soluble, inorganic builder. The water-soluble organic builders include polycarboxylic acids, in particular citric acid, adipic acid, succinic acid, glutaric acid, malic acid, tartaric acid, maleic acid, fumaric acid and saccharic acids, monomeric and polymeric aminopolycarboxylic acids, in particular methylglycinediacetic acid, nitrilotriacetic acid and ethylenediaminetetraacetic acid, and polyaspartic acid, polyphosphonic acids, in particular aminotris(methylenephosphonic acid), ethylenediaminetetrakis(methylenephosphonic acid) and 1-hydroxyethane-1,1-diphosphonic acid, polymeric hydroxy compounds such as dextrin, and polymeric (poly)carboxylic acids, polymeric acrylic acids, methacrylic acids, maleic acids and mixed polymers thereof, which may also contain, in the polymer, small proportions of polymerizable substances without a carboxylic acid functionality.

Compounds of this class which are suitable, although less preferred, are copolymers of acrylic acid or methacrylic acid with vinyl ethers, such as vinyl methyl ethers, vinyl esters, ethylene, propylene and styrene, in which the proportion of the acid is at least 50 wt. %.

The organic builders may, in particular for the production of liquid textile treatment or cleaning agents, be used in the form of aqueous solutions, preferably in the form of 30 to 50 wt. % aqueous solutions. All indicated acids are generally used in the form of water-soluble salts thereof, in particular alkali salts thereof.

Preferred salts are salts of polycarboxylic acids, such as citric acid, adipic acid, succinic acid, glutaric acid, tartaric acid, saccharic acids and mixtures thereof.

Organic builders may, if desired, be contained in amounts of up to 40 wt. %, in particular up to 25 wt. %, and preferably from 1 wt. % to 8 wt. %. Amounts close to the stated upper limit are preferably used in paste-form or liquid, in particular water-comprising, compositions according to the invention. Laundry aftertreatment, such as softeners, may optionally also be free of organic builder.

A composition according to the invention suitable as a textile treatment or cleaning agent preferably contains at least one enzyme. Suitable as enzymes that can be used are those from the class of proteases, cutinases, amylases, pullulanases, hemicellulases, cellulases, lipases, oxidases and peroxidases, and mixtures thereof. Enzymatic active ingredients obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia* are particularly suitable. The optionally used enzymes may be adsorbed on carrier substances and/or embedded in coating substances to protect said enzymes from premature inactivation. The enzymes are, if desired, preferably contained in the agents in amounts no greater than 5 wt. %, in particular from 0.2 wt. % to 2 wt. %.

An optical brightener is preferably selected from the substance classes of distyrylbiphenyls, stilbenes, 4,4'-diamino-2,2'-stilbenedisulfonic acids, coumarins, dihydroquinolinones, 1,3-diarylpyrazolines, naphthalic acid imides, benzoxazole systems, benzisoxazole systems, benzimidazole systems, pyrene derivatives substituted by heterocyclene and mixtures thereof.

Particularly preferred optical brighteners include disodium-4,4'-bis-(2-morpholino-4-anilino-s-triazin-6-ylamino) stilbenedisulfonate (which are available, for example, as Tinopal® DMS from BASF SE), disodium-2,2'-bis-(phenylstyryl)disulfonate (which are available, for example, as Tinopal® CBS from BASF SE), 4,4'-bis\[(4-anilino-6-\[bis (2-hydroxyethyl)amino]-1,3,5-triazin-2-yl)amino]stilbene-2,2'-disulfonic acid (which are available, for example, as Tinopal® UNPA from BASF SE), hexasodium-2,2'-\[vinylenebis\[(3-sulfonato-4,1-phenylene)imino\[6-(diethyl-amino)-1,3,5-triazine-4,2-diyl]imino]]bis-(benzene-1,4-disulfonate) (which are available, for example, as Tinopal® SFP from BASF SE), 2,2'-(2,5-thiophenediyl)bis\[5-1,1-dimethylethyl)benzoxazole (which are available, for example, as Tinopal® SFP from BASF SE) and/or 2,5-bis(benzoxazol-2-yl)thiophene.

In addition, the compositions according to the invention suitable as textile treatment or cleaning agents may also contain components that positively influence the capability for washing out oil and grease from textiles, or what are referred to as soil release active ingredients. This effect is particularly apparent when a textile is soiled which has been previously washed several times using an agent that contains this deoiling and degreasing component. Preferred deoiling and degreasing components include, for example, nonionic cellulose ethers such as methyl cellulose and methylhydroxypropyl cellulose having a proportion of from 15 to 30 wt. % methoxyl groups and from 1 to 15 wt. % hydroxypropoxyl groups, in each case based on the nonionic cellulose ether, and the polymers of phthalic acid and/or terephthalic acid known from the prior art, or derivatives thereof, with monomeric and/or polymeric diols, in particular polymers of ethylene terephthalates and/or polyethylene glycol terephthalates or anionically and/or nonionically modified derivatives thereof.

The textile treatment or cleaning agents may also contain dye transfer inhibitors, preferably in amounts of from 0.1 wt. % to 2 wt. %, in particular from 0.1 wt. % to 1 wt. %, which, in a preferred embodiment of the invention, are polymers of vinylpyrrolidone, vinylimidazole or vinylpyridine-N-oxide, or copolymers thereof.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides comprising acidic groups are also suitable for this purpose. Starch derivatives other than those mentioned above may also be used, for example aldehyde starches. Cellulose ethers, such as carboxymethyl cellulose (Na salt), methyl cellulose, hydroxyalkyl cellulose, and mixed ethers, such as methylhydroxyethyl cellulose, methylhydroxypropyl cellulose, methylcarboxymethyl cellulose and mixtures thereof, may preferably be used, for example, in amounts of from 0.1 to 5 wt. %, based on the agents.

It is preferred for the dye transfer inhibitor to be a polymer or copolymer of cyclic amines, such as vinylpyrrolidone and/or vinylimidazole. Polymers suitable as dye transfer inhibitors include polyvinylpyrrolidone (PVP), polyvinylimidazole (PVI), copolymers of vinylpyrrolidone and vinylimidazole (PVP/PVI), polyvinylpyridine-N-oxide, poly-N-carboxymethyl-4-vinylpyridium chloride, polyethylene glycol-modified copolymers of vinylpyrrolidone and vinylimidazole, and mixtures thereof. Polyvinylpyrrolidone (PVP), polyvinylimidazole (PVI) or copolymers of vinylpyrrolidone and vinylimidazole (PVP/PVI) are particularly preferably used as a dye transfer inhibitor. The used polyvinylpyrrolidones (PVP) preferably have an average molecular weight of from 2,500 to 400,000, and are commercially available from ISP Chemicals as PVP K 15, PVP K 30, PVP K 60 or PVP K 90 or from BASF as Sokalan® HP 50 or Sokalan® HP 53. The used copolymers of vinylpyrrolidone and vinylimidazole (PVP/PVI) preferably have a molecular weight in the range of from 5,000 to 100,000. A PVP/PVI copolymer is commercially available, for example, from BASF under the name Sokalan® HP 56. Further highly preferred dye transfer inhibitors that can be used are polyethylene glycol-modified copolymers of vinylpyrrolidone and vinylimidazole, which are available, for example, from BASF under the name Sokalan® HP 66.

According to the invention, it is preferred for the liquid composition according to the invention to additionally contain at least one thickener, preferably at least one copolymer of an ethylenically unsaturated carboxylic acid.

The thickener is preferably contained in an amount of from 0.05 wt. % to 2 wt. %, particularly preferably from 0.1 wt. % to 1 wt. %, very particularly preferably from 0.4 wt. % to 0.6 wt. %.

It is particularly preferred for the composition according to the invention to contain at least one polymeric thickener. A polymeric thickener is a polymer having a thickening effect and an average molecular weight (MW) of at least 1,000 g/mol. The polymeric thickener is preferably contained in an amount of from 0.05 wt. % to 2 wt. %, particularly preferably from 0.1 wt. % to 1 wt. %, very particularly preferably from 0.4 wt. % to 0.6 wt. %.

Suitable polymeric thickeners are preferably polymers, in particular copolymers, of an ethylenically unsaturated carboxylic acid (in particular polymers or copolymers of acrylic acid, polymers or copolymers of methacrylic acid or mixtures thereof), polysaccharides such as starch, hydroxyalkyl starch, cellulose, hydroxyalkyl cellulose. Said copolymers of an ethylenically unsaturated carboxylic acid are, for example, selected from polyalkenyl polyethers, in particular allyl ethers of saccharose or pentaerythrite-crosslinked homopolymers of acrylic acid (INCI declaration according to the "International Dictionary of Cosmetic Ingredients" from the "The Cosmetic, Toiletry and Fragrance Association (CTFA)": Carbomer). Crosslinked polyacrylic acids of this kind are available from the 3V Sigma as Polygel®, e.g. Polygel DA, and from Noveon as Carbopol®, e.g. Carbopol 940 (MW of approx. 4,000,000), Carbopol 941 (MW of approx. 1,250,000) or Carbopol 934 (MW of approx. 3,000,000).

Preferred copolymers of an ethylenically unsaturated carboxylic acid are selected from: copolymers of two or more monomers, selected from acrylic acid, methacrylic acid and esters thereof with $C_{1-4}$ alkanols (INCI Acrylates Copolymer), particularly preferably copolymers of methacrylic acid, butyl acrylate and methyl methacrylate (CAS number according to the Chemical Abstracts Service: 25035-69-2) or copolymers of butyl acrylate and methyl methacrylate (CAS 25852-37-3), which are available, for example, from Rohm & Haas as Aculyn® and Acusol® or from Evonik (Goldschmidt) as Tego® Polymer, e.g. anionic and non-associative polymers Aculyn 33 (crosslinked), Acusol 810, Acusol 823 and Acusol 830 (CAS 25852-37-3); crosslinked acrylic acid copolymers, in particular copolymers of $C_{10-30}$ alkyl acrylate with one or more monomers, selected from acrylic acid, methacrylic acid and esters thereof with $C_{1-4}$ alkanols, crosslinked by an allyl ether of saccharose or of pentaerythrite (INCI Acrylates/$C_{10-30}$ Alkyl Acrylate Crosspolymer), which are available, for example, from Noveon as Carbopol®, e.g. hydrophobized Carbopol ETD 2623 and Carbopol 1382 (INCI Acrylates/$C_{10-30}$ Alkyl Acrylate Crosspolymer) or Carbopol Aqua 30 (formerly Carbopol EX 473).

Very particularly preferably, the composition according to the invention contains at least one polymeric thickener, which is obtained by copolymerizing at least the following monomers: (i) acrylic acid or methacrylic acid, (ii) at least one ester of acrylic acid with a $C_{1-4}$ alkanol and/or at least one ester of methacrylic acid with a $C_{1-4}$ alkanol, (iii) optionally at least one monomer of formula (M1)

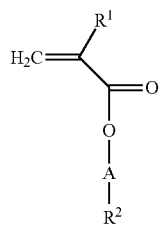

where
$R^1$ represents a hydrogen atom or a methyl group,
$R^2$ represents a ($C_8$-$C_{30}$) alkyl group, A represents a group *—$(CH_2CH_2O)_x$—* where X represents an integer from 5 to 35, a group *—$(CH_2CHMeO)_y$—* where y represents an integer from 5 to 35, or a group *—$(CH_2CH_2O)_x$—$(CH_2CHMeO)_y$—* where the sum x+y represents an integer from 5 to 35 and x and y are greater than zero.

Preferred polymeric thickeners from the group of polysaccharides are selected from at least one compound from the group formed of starch, dextrin, carboxymethyl starch, cellulose, carboxymethyl cellulose, hydroxyethyl cellulose, xanthan gum, carrageenan, guar gum and gum arabic.

According to the invention, it is very particularly preferred for the composition according to the invention to contain, as a thickener, at least one polymeric thickener selected from copolymers of at least one ethylenically unsaturated carboxylic acid, and at least one polymeric thickener selected from polysaccharide. In this case it is in turn preferred for the composition according to the invention to contain, as a thickener, (a) at least one polymeric thickener, which is obtained by polymerizing (i) acrylic acid or methacrylic acid, (ii) at least one ester of acrylic acid with a $C_{1-4}$ alkanol and/or at least one ester of methacrylic acid with a $C_{1-4}$ alkanol, and (iii) preferably at least one monomer of the above formula (M1), and (b) at least one polymeric thickener selected from starch, dextrin, carboxymethyl starch, cellulose, carboxymethyl cellulose, hydroxyethyl cellulose, xanthan gum, carrageenan, guar gum and gum arabic, or mixtures thereof.

According to the invention, it is preferred for the composition according to the invention to additionally contain at least one inorganic salt. The inorganic salt is particularly preferably contained in an amount of from 0.1 to 1.5 wt. %, in particular from 0.2 to 1.2 wt. %, very particularly preferably from 0.3 to 1.0 wt. %. Preferred inorganic salts are selected from inorganic salts of monovalent metal cations. Particularly preferred inorganic salts are sodium chloride, sodium sulfate, potassium chloride, potassium sulfate or mixtures thereof.

According to the invention, preferred compositions additionally contain (a) at least one polymeric thickener, which is obtained by polymerizing (i) acrylic acid or methacrylic acid, (ii) at least one ester of acrylic acid with a $C_{1-4}$ alkanol and/or at least one ester of methacrylic acid with a $C_{1-4}$ alkanol, and (iii) preferably at least one monomer of the above formula (M1), and (b) at least one polymeric thickener selected from polysaccharide, in particular from starch, dextrin, carboxymethyl starch, cellulose, carboxymethyl cellulose, hydroxyethyl cellulose, xanthan gum, carrageenan, guar gum and gum arabic, or mixtures thereof, and (c) at least one inorganic salt.

In particular, low-water or water-free liquid compositions according to the invention may be in preportioned form, the composition according to the invention being filled into a water-soluble wrapping and it thus being possible for said composition to be part of a water-soluble packaging. If the composition according to the invention is packaged in a water-soluble wrapping, it is preferred for the water content to be less than 10 wt. %, based on the overall agent, and for anionic surfactants, if present, to be in the form of ammonium salts thereof.

It has been found that the transparent, liquid compositions according to the invention, in particular if comprising at least one thickener, are highly suitable as a continuous phase for producing a suspension of optical effect solids. A second subject of the invention is therefore a suspension of optical effect solids, selected from pearlescing pigments, speckles, dye pigments and mixtures thereof. This suspension is optically more appealing than a suspension which has conventional perfume microcapsules without said odor modulator compound and of which the fragrancing capacity is of the same acceptable standard.

Pearlescing pigments are pigments that have a nacreous shine. Pearlescing pigments consist of thin sheets that have a high refractive index and partly reflect, and are partly transparent to, light. The nacreous shine is produced by interference of the light striking the pigment (interference pigment). Pearlescing pigments are generally thin sheets of the above-mentioned material, or contain the above-mentioned material as thin multilayer films or as components arranged in parallel in a suitable carrier material.

The pearlescing pigments that can be used according to the invention are either natural pearlescing pigments, e.g. fish silver (guanine/hypoxanthine mixed crystals from fish scales) or nacre (from ground mussel shells), monocrystalline sheet-like pearlescing pigments, such as bismuth oxychloride, and pearlescing pigments based on mica and mica/metal oxide. The latter pearlescing pigments are micas that have been provided with a metal oxide coating.

By using the pearlescing pigments in the suspension according to the invention, shine and optionally also color effects are achieved.

Pearlescing pigments based on mica and mica/metal oxide are preferred according to the invention. Mica is a phyllosilicate. The most important representatives of these silicates are muscovite, phlogopite, paragonite, biotite, lepidolite and margarite. Mica, primarily muscovite or phlogopite, is coated with a metal oxide in order to produce the pearlescing pigments in conjunction with metal oxides. Suitable metal oxides are, inter alia, $TiO_2$, $Cr_2O_3$ and $Fe_2O_3$. Interference pigments and colored luster pigments are obtained, as pearlescing pigments according to the invention, by coating in a suitable manner. These types of pearlescing pigments also have color effects in addition a glittering optical effect. Furthermore, the pearlescing pigments that can be used according to the invention may also contain a color pigment that is not derived from a metal oxide.

The particle size of the preferably used pearlescing pigments is preferably of an average diameter $X_{50.3}$ (volume average) of between 1.0 and 100 µm, particularly preferably between 10.0 and 60.0 µm.

Within the meaning of the invention, speckles are understood to mean microcapsules which have an average diameter $X_{50.3}$ (volume average) of more than 300 m, in particular from 300 to 1,500 µm, preferably from 400 to 1,000 µm. Speckles are preferably matrix capsules. The matrix is preferably colored. The matrix formations takes place, for example, by gelification, polyanion/polycation interactions or polyelectrolyte/metal ion interactions, and is well known in the prior art, just as the production of the particles using these matrix-forming materials is. A matrix-forming material given by way of example is alginate. In order to produce alginate-based speckles, an aqueous alginate solution, optionally additionally comprising the active ingredient(s) to be included, is dropped and then precipitation-hardened in a precipitation bath comprising $Ca^{2+}$ ions or $Al^{3+}$ ions. Alternatively, different matrix-forming materials may be used instead of alginate.

A third subject of the invention is a method for fragrancing a substrate (in particular textiles), in which method the composition of the first or second subject of the invention is brought into contact with the substrate (in particular textiles), optionally as a dilution. According to the invention, it is particularly preferred for 10 to 200 ml, in particular 20 to 150 ml, of the composition of the first and second subjects of the invention to be diluted with 5 to 50 l of a solvent, preferably water, and for the substrate to be brought into contact with the resultant diluted application mixture.

The method according to the invention is particularly preferably a textile treatment method in which textiles are introduced into a washing machine, in particular of a home washing machine, the composition of the first or second subject of the invention for producing a diluted, aqueous application mixture is introduced into said washing machine, and the textiles come into contact with said application mixture.

During the washing cycle and/or rinsing stage, the textiles may come into contact with the composition of the first of second subject of the invention.

Preferred embodiments of the invention are illustrated by the following points:

1. A liquid, transparent composition, in particular as a textile treatment agent, comprising
a) at least one odorant
and
b) from 0.00001 to 0.2 wt. % microcapsules, comprising at least one odor modulator compound, wherein each individual modulator compound
   i) is contained, based on the total of all the odorants contained in the composition, in an amount of from 2 wt. % to 0.000001 wt. %, and
   ii) contains at least one heteroatom, wherein the at least one heteroatom is selected from N, O, S, Si, Se, F, Cl, Br or I, and
   iii) has a molecular weight of lower than 250 g mol$^{-1}$, and
wherein the composition has an efficiency factor of at least 1.15 on account of the at least one odor modulator compound, wherein the efficiency factor is calculated according to the following formula:

$$E = \frac{P_{GMV}}{P+1} \geq 1.15$$

where E=efficiency factor and P=number of persons trained in odors that deemed the composition having an odor modulator compound ($P_{GMV}$) or not having an odor modulator compound (P) to be more intense, wherein the sum of $P_{GMV}$ and P is at least 34.

2. The composition according to point 1, characterized in that the at least one odor modulator compound is selected from 2-acetylpyridine (CAS no. 1122-62-9), 2,5-dimethylpyrazine (CAS no. 123-32-0), ethyl 3-methylthiopropionate (CAS no. 13327-56-5), methyl 3-methylthiopropionate (CAS no. 13532-18-8), 2,3,5-trimethylpyrazine (CAS no. 1466755-1), 2-ethyl-4-methylthiazole (CAS no. 15679-12-6), 2-isopropyl-4-methylthiazole (CAS no. 15679-13-7), 2-ethyl-3-methylpyrazine (CAS no. 15707-23-0), 2-isobutylthiazole (CAS no. 1864074-9), ethyl 2-mercaptopropionate (CAS no. 19788-49-9), 2-acetylpyrazine (CAS no. 22047-25-2), 4-methylthio-4-methylpentan-2-one (CAS no. 23550-40-5), 2-acetyl-3-methylpyrazine (CAS no. 23787-80-6), 2-acetylthiazole (CAS no. 24295-03-2), S-methyl butanethioate (CAS no. 2432-51-1), 2-isobutyl-3-methoxypyrazine (CAS no. 24683-00-9), 2,2'-(dithiodimethylene)difuran (CAS no. 4437-20-1), 3-methylthio-1-hexanol (CAS no. 51755-66-9), 3-mercapto-1-hexanol (CAS no. 51755-83-0), dibutyl sulfide (CAS no. 544-40-1), 2,3-dimethylpyrazine (CAS no. 5910-89-4), 1-para-menthene-8-thiol (CAS no. 71159-90-5), 2-mercaptopropionic acid (CAS no. 79-42-5), 2,2,4,4,6,6-hexamethyl-1,3,5-trithiane (CAS no. 828-26-2), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)-ethanone (CAS no. 1646-26-0), nerolione (CAS no. 23911-56-0), methyl corylone (CAS no. 13494-06-9), sotolone (CAS no. 28664-35-9), furaneol methyl ether (CAS no. 4077-47-8), emoxyfurone (CAS no. 698-10-2), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4.8-dimethyl-3,7nonadienyl)pyridine (CAS no. 3846223-6), 5-hexyl-2-methylpyridine (CAS no. 710-40-7), thiomenthone (CAS no. 38462-22-5), thiocineol (CAS no. 68398-18-5), sulfurol (CAS no. 137-00-8), benzothiazole (CAS no. 95-16-9), 4,5-dihydro-3(2H)thiophenone (CAS no. 1003-04-9), 2-hydroxy-2-cyclohexen-1-one (CAS no. 10316-66-2), 3-acetyl-2,5-dimethylfurane (CAS no. 10599-70-9), 2-propionylpyrrole (CAS no. 1073-26-3), 2-(methylthio)phenol (CAS no. 1073-29-6), methyl 2-furfurylthioacetate (CAS no. 108499-33-8), furfurylideneacetone (CAS no. 108811-61-6), natural pyrazine mixture (CAS no. 84082-50-8), 1-pentanethiol (CAS no. 110-66-7), 2-methoxycinnamyl acetate (CAS no. 110823-66-0), dipropyl sulfide (CAS no. 111-47-7), 2,3,5,6-tetramethylpyrazine (CAS no. 1124-11-4), 2-hexylpyridine (CAS no. 1129-69-7), 4-butyroxy-2,5-dimethyl-3(2H)-furanone (CAS no. 114099-96-6), 2,6-dimethylthiophenol (CAS no. 118-72-9), 2-methylheptanoic acid (CAS no. 1188-02-9), 1,6-hexanedithiol (CAS no. 1191-43-1), 2-acetylfuran (CAS no. 1192-62-7), 2-acetyl-5-methylfuran (CAS no. 1193-79-9), 2,4,5-trimethylthiazole (CAS no. 13623-11-5), 1-(methylthio)-2-butanone (CAS no. 13678-58-5), 2-methyl-5-thiomethylfuran (CAS no. 13678-59-6), furfuryl thioacetate (CAS no. 13678-68-7), 3-thiohexylacetate (CAS no. 136954-20-6), 3-mercaptohexylbutyrate (CAS no. 136954-21-7), 3-mercaptohexylhexanoate (CAS no. 136954-22-8), 3-acetylthiohexylacetate (CAS no. 136954-25-1), 2-thiocresol (CAS no. 137-06-4), 2-ethylpyrazine (CAS no. 13925-00-3), 1-methylthio-2-propanone (CAS no. 14109-72-9), 3-(2-methylpropyl)pyridine (CAS no. 14159-61-6), furfuryl methyl sulfide (CAS no. 1438-91-1), 1-(2-furanylmethyl)-1H-pyrrole (CAS no. 1438-94-4), 2-butylthiophene (CAS no. 1455-20-5), S-methyl thioacetate (CAS no. 1534-08-3), 2,3-diethylpyrazine (CAS no. 15707-24-1), 2-methyl-3-propylpyrazine (CAS no. 15986-80-8), 2,3-dihydro-5,6-dimethylpyrazine (CAS no. 15986-92-2), bis-(methylthio)methane (CAS no. 1618-26-4), 3-methylthiobutanal (CAS no. 16630-52-7), 3-(methylthio)propylacetate (CAS no. 16630-55-0), 3-(methylthio)propyl butyrate (CAS no. 16630-60-7), methyl (methylthio)acetate (CAS no. 16630-66-3), 4-methyl-5-vinylthiazole (CAS no. 1759-28-0), 2,3-diethyl-5-methylpyrazine (CAS no. 18138-04-0), 2-(1-methylpropyl)thiazole (CAS no. 18277-27-5), 2-methylbutane-1-thiol (CAS no. 1878-18-8), 2-hexylthiophene (CAS no. 18794-77-9), furfuryl isopropyl sulfide (CAS no. 1883-78-9), 4-methyl-4-mercapto-pentan-2-one (CAS no. 19872-52-7), ethyl methyl disulfide (CAS no. 20333-39-5), diallyl trisulfide (CAS no. 2050-87-5), 4-methylthiobutanol (CAS no. 20582-85-8), 2,4,5-trimethyloxazole (CAS no. 20662-84-4), 3-methyl-2-butanethiole (CAS no. 2084-18-6), 2-pentanethiol (CAS no. 2084-19-7), 2-(3-phenylpropyl)pyridine (CAS no. 2110-18-1), diallyl disulfide (CAS no. 2179-57-9), allyl methyl sulfide (CAS no. 2179-58-0), allyl propyl disulfide (CAS no. 2179-59-1), 2,3-dithiahexane (CAS no. 2179-60-4), 2,4,5-trimethyl-3-oxazoline (CAS no. 22694-96-8), 2-pentylpyridine (CAS no. 2294-76-0), 2-methylthioacetaldehyde (CAS no. 23328-62-3), 2-methyl-2-thiazoline (CAS no. 2346-00-1), 3,5-dimethyl-1,2,4-trithiolane (CAS no. 23654-92-4), 5-methyl-6,7-dihydrocyclopentapyrazine (CAS no. 23747-48-0), 2-methylthiazolidine (CAS no. 24050-16-6), 2-methyltetrahydrofuran-3-thioacetate (CAS no. 252736-41-7), 2-methyl-3-furanthiol (CAS no. 28588-74-1), bis-(2-methyl-3-tetrahydrofuran)disulfide (CAS no. 28588-75-2), 3-methylcyclohexane-1,2-dione (CAS no. 3008-43-3), ethyl propyl disulfide (CAS no. 30453-31-7), 3(5-methyl-2-furyl)butanal (CAS no. 31704-80-0), 2-methyltetrahydrofuran-3-one (CAS no. 318800-9), 2-pentanoylfuran (CAS no. 3194-17-0), 2-ethylfuran (CAS no. 3208-16-0), 3-methylthiopropanal (CAS no. 3268-49-3), 2-acetyl-3-ethylpyrazine (CAS no. 32974-92-8), 4-(methylthio)-2-butanone (CAS no. 34047-39-7), 3-acetylpyridine (CAS no. 350-03-8), 2-pyrazineethanethiol (CAS no. 35250-53-4), 4,5-dimethylthiazole (CAS no. 3581-91-7), 2-pentylfuran (CAS no. 3777-69-3), 2-heptylfuran (CAS no. 3777-71-7), 5-acetyl-2,4-dimethylthiazole (CAS no. 38205-60-6), 3-methylthiohexanal (CAS no. 38433-74-8), thiogeraniol (CAS no. 39067-80-6), 2-ethyl-5-methylthiophene (CAS no. 40323-88-4), 3-mercapto-2-butanone (CAS no. 40789-98-8), 3-methylthiopropylamine (CAS no. 4104-45-4), 4-acetoxy-2,5-dimethyl-3(2H)-furanone (CAS no. 4166-20-5), S-methyl 2-methylbutanethioate (CAS no. 42075-45-6), 2-propylfuran (CAS no. 4229-91-8), diisopropyl disulfide (CAS no. 4253-89-8), 2-propionylthiazole (CAS no. 43039-98-1), 2-phenylethanethiol (CAS no. 4410-99-5), ethyl 2-(methylthio)acetate (CAS no. 4455-13-4), 2-butylfuran (CAS no. 4466-24-4), 2-ethylthiophenol (CAS no. 4500-58-7), 2-pentylthiophene (CAS no. 4861-58-9), ethyl 2-methyl-2-methylthiopropionate (CAS no. 49773-24-2), 2-(ethylthio)-1-propanol (CAS no. 72311-96-7), 3-methylthiopropanol (CAS no. 505-10-2), 3-methylthiopropylisothiocyanate (CAS no. 505-79-3), thioacetic acid (CAS no. 50709-5), methyl 2-(methylthio)butyrate (CAS no. 51534-66-8), 3-methylthio-hex-1-ylacetate (CAS no. 51755-85-2), 2-(methylthio)ethanol (CAS no. 5271-38-5), methyl 4-methylthiobutyrate (CAS no. 53053-51-3), 2-isobutyl-4,5-dimethylthiazole (CAS no. 53498-32-1), 3-ethylpyridine (CAS no. 53678-7), 2-ethyl-4,5-dimethyloxazole (CAS no. 53833-30-0), 2.4-dimethylthiazole (CAS no. 541-58-2), 2-butyl-5-ethylthiophene (CAS no. 54411-06-2), 2,4,6-triethyldihydro-1,3,5-dithiazine (CAS no. 54717-17-8), 3-mercapto-2-butanol (CAS no. 54812-86-1), 2-ethyl-3 (5/6)-dimethylpyrazine (CAS no. 55031-15-7), 2-methyl-1,3-dithiolane (CAS no. 5616-51-3), 2-methyltetrahydrofuran-3-thiol (CAS no. 57124-87-5), 3,5,5-trimethylcyclohexane-1,2-dione (CAS no. 57696-89-6), 1.2-cyclohexanediol (CAS no. 57794-08-8), furfuryl thiopropionate (CAS no. 59020-85-8), furfuryl thioformate (CAS no. 59020-90-5), dipropyl trisulfide (CAS no. 6028-61-1), S-methyl-4-methyl pentanethioate (CAS no. 61122-71-2), 5-methylfurfural (CAS no. 620-02-0), 2-propylpyridine (CAS no. 622-39-9), furfuryl acetate (CAS no. 623-17-6), 3-(2-furyl)acrolein (CAS no. 623-30-3), dimethyl disulfide (CAS no. 624-92-0), ethyl thioacetate (CAS no. 625-60-5), 2-thienylmercaptan (CAS no. 6258-63-5), 1-phenylethanethiol (CAS no. 6263-65-6), n-butyl methyl sulfide (CAS no. 628-29-5), dipropyl disulfide (CAS no. 629-19-6), 2-isobutylpyridine (CAS no. 6304-24-1), 2,5-dimethylthiophene (CAS no. 638-02-8), 2,4,6-trithiaheptane (CAS no. 6540-86-9), 4-methyl-5-thiazolethanolacetate (CAS no. 656-53-1), 2-(sec-butyl)-4,5-dimethyl-3-thiazoline (CAS no. 65894-82-8), 2-isobutyl-4,5-dimethyl-3-thiazoline (CAS no. 65894-83-9), 4-allyl-2,6-dimethoxyphenol (CAS no. 6627-88-9), 3-mercapto-2-pentanone (CAS no. 67633-97-0), 2-methyl-4-propyl-1,3-oxathiane (CAS no. 59323-76-1), 2-methylthio-3(5/6) methylpyrazine (CAS no. 67952-65-2), 4-methylthiazole (CAS no. 693-95-8), 2-furyl-2-propanone (CAS no. 6975-60-6), benzyl methyl disulfide (CAS no. 699-10-5), amyl methyl disulfide (CAS no. 72437-68-4), 2-methylquinoxaline (CAS no. 7251-61-8), 2-acetyl-3,5(6)-dimethylpyrazine (CAS no. 72797-17-2), diallyl polysulfide (CAS no. 72869-75-1), ethyl 2-methoxybenzoate (CAS no. 7335-26-4), methyl thiomethyl hexanoate (CAS no. 74758-91-1), methyl thiomethyl butyrate (CAS no. 74758-93-3), methyl mercaptan (CAS no. 74-93-1), benzyl methyl sulfide (CAS no. 766-92-7), 2-ethyl-4,5-dimethylthiazoline (CAS no. 76788-46-0), 2-methoxy-4-vinylphenol (CAS no. 7786-61-0), allyl mercaptan (CAS no. 870-23-5), 2-methyl-3-(2-furyl)prop-2-enal (CAS no. 874-66-8), 2-octylthiophene (CAS no. 880-36-4), 1,5-pentanedithiol (CAS no. 928-98-3), isoamyl 3-methylthiopropionate (CAS no. 93762-35-7), ethyl 3-(furfurylthiol)propionate (CAS no. 94278-27-0), para-mentha-8-thioacetat-3-one (CAS no. 94293-57-9), furfuryl alcohol (CAS no. 98-00-0), 3-acetyl-2,5-dimethylthiophene (CAS no. 2530-10-1), ethyl 2-methylbutyrate (CAS no. 7452-79-1), decenal-4-trans (CAS no. 65405-70-1).

3. The composition according to point 1 or 2, characterized in that the at least one odor modulator compound is selected from 2-acetylpyridine (CAS no. 1122-62-9), 2,5-dimethylpyrazine (CAS no. 123-32-0), ethyl 3-methylthiopropionate (CAS no. 13327-56-5), methyl 3-methylthiopropionate (CAS no. 13532-18-8), 2,3,5-trimethylpyrazine (CAS no. 14667-55-1), 2-ethyl-4-methylthiazole (CAS no. 15679-12-6), 2-isopropyl-4-methylthiazole (CAS no. 15679-13-7), 2-ethyl-3-methylpyrazine (CAS no. 15707-23-0), 2-isobutylthiazole (CAS no. 18640-74-9), ethyl 2-mercaptopropionate (CAS no. 19788-49-9), 4-methylthio-4-methyl-2-pentanone (CAS no. 23550-40-5), 2-acetylpyrazine (CAS no. 22047-25-2), 2-acetyl-3-methylpyrazine (CAS no. 23787-80-6), 2-acetylthiazole (CAS no. 24295-03-2), S-methyl butanethioate (CAS no. 2432-51-1), 2-isobutyl-3-methoxypyrazine (CAS no. 24683-00-9), 2,2'-(dithiodimethylene)difuran (CAS no. 4437-20-1), 3-methylthio-1-hexanol (CAS no. 5175566-9), 3-mercapto-1-hexanol (CAS no. 51755-83-0), dibutyl sulfide (CAS no. 544-40-1), 2,3-dimethylpyrazine (CAS no. 5910-89-4), 1-para-menthene-8-thiol (CAS no. 71159-90-5), 2,2,4,4,6,6-hexamethyl-1,3,5-trithiane (CAS no. 828-26-2), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), methyl corylone (CAS no. 13494-06-9), sotolone (CAS no. 28664-35-9), furaneol methyl ether (CAS no. 4077-47-8), emoxyfurone (CAS no. 698-10-2), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4.8-Dimethyl-3,7nonadienyl)pyridine (CAS no. 3846223-6), 5-hexyl-2-methylpyridine (CAS no. 710-40-7), thiomenthone (CAS no. 38462-22-5), thiocineol (CAS no. 68398-18-5), sulfurol (CAS no. 137-00-8), benzothiazole (CAS no. 95-16-9), ethyl 2-methylbutyrate (CAS no. 7452-79-1), decenal-4-trans (CAS no. 65405-70-1).

4. The composition according to point 1, comprising at least one odor modulator compound of general formula (I),

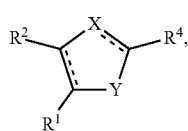

Formula (I)

where
X represents nitrogen, sulfur or $CR^3$; and
X represents oxygen, sulfur or $NR^5$; and $R^1$, $R^2$ and $R^5$ each represent, independently of one another, hydrogen or functional groups having 1 to 6 carbon atoms; and $R^3$ and $R^4$ each represent, independently of one another, hydrogen or functional groups having 1 to 9 carbon atoms, where
the ring of formula (I) may contain, at the positions linked by dashed lines, each independently of one another, double bonds, with the proviso that the at least one odor modulator compound, if X represents nitrogen, contains a double bond between X and the carbon atom of the ring of formula (I) that is linked to $R^4$; and the carbon atoms of the ring of formula (I) that are linked to $R^1$ and $R^2$ may together be part of an annulated five-member or six-member ring, where functional groups $R^1$ and $R^2$ are each, independently of one another, an integral part of the annulated ring either completely or in part;

and
one or more methyl groups, methylene groups, methine groups or quaternary carbon atoms of functional groups $R^1$ to $R^5$ may each, independently of one another, be substituted by heteroatoms.

5. The composition according to point 4, characterized in that the at least one odor modulator compound is selected from 2-ethyl-4-methylthiazole (CAS no. 15679-12-6), 2-isopropyl-4-methylthiazole (CAS no. 15679-13-7), 2-isobutylthiazole (CAS no. 18640-74-9), 2-acetylthiazole (CAS no. 24295-03-2), 2,2'-(dithiodimethylene)difuran (CAS no. 4437-20-1), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)-ethanone (CAS no. 164626-0), nerolione (CAS no. 23911-56-0), furfural propylene glycol acetal (CAS no. 4359-54-0), furaneol methyl ether (CAS no. 4077-47-8), sulfurol (CAS no. 137-00-8), benzothiazole (CAS no. 95-16-9), 4,5-dihydro-3(2H)thiophenone (CAS no. 1003-04-9), 3-acetyl-2,5-dimethylfuran (CAS no. 10599-70-9), 2-propionylpyrrole (CAS no. 1073-26-3), methyl 2-furfurylthioacetate (CAS no. 108499-33-8), furfurylideneacetone (CAS no. 108811-61-6), 4-butyroxy-2,5-dimethyl-3(2H)-furanone (CAS no. 114099-96-6), 2-acetylfuran (CAS no. 1192-62-7), 2-acetyl-5-methylfuran (CAS no. 1193-79-9), 2,4,5-trimethylthiazole (CAS no. 13623-11-5), 2-methyl-5-thiomethylfuran (CAS no. 13678-59-6), furfuryl thioacetate (CAS no. 13678-68-7), furfuryl methyl sulfide (CAS no. 1438-91-1), 1-(2-furanylmethyl)-1H-pyrrole (CAS no. 1438-94-4), 2-butylthiophene (CAS no. 1455-20-5), 4-methyl-5-vinylthiazole (CAS no. 1759-28-0), 2-(1-methylpropyl)thiazole (CAS no. 18277-27-5), 2-hexylthiophene (CAS no. 18794-77-9), furfuryl isopropyl sulfide (CAS no. 1883-78-9), 2,4,5-trimethyloxazole (CAS no. 20662-84-4), 2-methyl-2-thiazoline (CAS no. 2346-00-1), 2-methylthiazolidine (CAS no. 24050-16-6), 2-methyltetrahydrofuran-3-thioacetate (CAS no. 252736-41-7), 2-methyl-3-furanthiol (CAS no. 28588-74-1), bis-(2-methyl-3-tetrahydrofuran) disulfide (CAS no. 28588-75-2), 3(5-methyl-2-furyl)butanal (CAS no. 31704-80-0), 2-methyltetrahydrofuran-3-one (CAS no. 3188-00-9), 2-pentanoylfuran (CAS no. 3194-17-0), 2-ethylfuran (CAS no. 3208-16-0), 4,5-dimethylthiazole (CAS no. 3581-91-7), 2-pentylfuran (CAS no. 3777-69-3), 2-heptylfuran (CAS no. 3777-71-7), 5-acetyl-2,4-dimethylthiazole (CAS no. 38205-60-6), 2-ethyl-5-methylthiophene (CAS no. 4032388-4), 4-acetoxy-2,5-dimethyl-3(2H)-furanone (CAS no. 4166-20-5), 2-propylfuran (CAS no. 4229-91-8), 2-propionylthiazole (CAS no. 43039-98-1), 2-butylfuran (CAS no. 4466-24-4), 2-pentylthiophene (CAS no. 4861-58-9), 2-isobutyl-4,5-dimethylthiazole (CAS no. 53498-32-1), 2-ethyl-4,5-dimethyloxazole (CAS no. 53833-30-0), 2,4-dimethylthiazole (CAS no. 541-58-2), 2-butyl-5-ethylthiophene (CAS no. 54411-06-2), 2-methyl-1,3-dithiolane (CAS no. 5616-51-3), 2-methyltetrahydrofuran-3-thiol (CAS no. 57124-87-5), furfuryl thiopropionate (CAS no. 59020-85-8), furfuryl thioformate (CAS no. 59020-90-5), 5-methylfurfural (CAS no. 620-02-0), furfuryl acetate (CAS no. 623-17-6), 3-(2-furyl)acrolein (CAS no. 623-30-3), 2-thienylmercaptan (CAS no. 6258-63-5), 2,5-dimethylthiophene (CAS no. 638-02-8), 4-methyl-5-thiazolethanolacetate (CAS no. 656-53-1), 4-methylthiazole (CAS no. 693-95-8), 2-furyl-2-propanone (CAS no. 6975-60-6), 2-methyl-3-(2-furyl)prop-2-enal (CAS no. 874-66-8), 2-octylthiophene (CAS no. 880-36-4), ethyl 3-(furfurylthiol) propionate (CAS no. 94278-27-0), furfuryl alcohol (CAS no. 98-00-0), 3-acetyl-2,5-dimethylthiophene (CAS no. 2530-10-1), 2-acetylpyrrole (CAS no. 1072-83-9).

6. The composition according to point 4 or 5, characterized in that the at least one odor modulator compound is selected from 2-ethyl-4-methylthiazole (CAS no. 15679-12-6), 2-isopropyl-4-methylthiazole (CAS no. 15679-13-7), 2-isobutylthiazole (CAS no. 18640-74-9), 2-acetylthiazole (CAS no. 24295-03-2), 2,2'-(dithiodimethylene)difuran (CAS no. 4437-20-1), furfuryl mercaptan (CAS no. 98-02-2), furfural propylene glycol acetal (CAS no. 4359-54-0), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), furaneol methyl ether (CAS no. 4077-47-8), sulfurol (CAS no. 137-00-8), benzothiazole (CAS no. 95-16-9), 2-acetylpyrrole (CAS no. 1072-83-9).

7. The composition according to point 1, comprising at least one odor modulator compound of general formula (II),

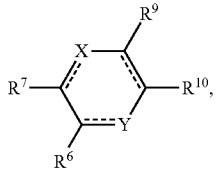

Formula (II)

where
X represents nitrogen or $CR^8$; and
Y represents nitrogen, $CR^{11}$ or $CR^{11}R^{12}$; and
$R^6$ and $R^8$ each represent, independently of one another, hydrogen or functional groups having 1 to 10 carbon atoms; and
$R^7$ and $R^9$ to $R^{12}$ each represent, independently of one another, hydrogen or functional groups having 1 to 4 carbon atoms,
where
the ring of formula (II) may contain, at the positions connected by dashed lines, each independently of one another, double bonds, with the proviso that the at least one odor modulator compound, if X or Y represents nitrogen, contains a double bond between X and the carbon atom of the ring of formula (II) that is linked to $R^7$, or between Y and the carbon atom of the ring of formula (II) that is linked to $R^6$, respectively; and
the carbon atoms of the ring of formula (II) that are linked to $R^6$ and $R^7$ may together be part of an annulated five-member or six-member ring, where functional groups $R^6$ and $R^7$ are each, independently of one another, an integral part of the annulated ring either completely or in part;
and
one or more methyl groups, methylene groups, methine groups or quaternary carbon atoms of functional groups $R^6$ to $R^{12}$ may each, independently of one another, be substituted by heteroatoms; and
if Y represents $CR^{11}R^{12}$, there is no double bond between Y and the carbon atom of the ring that is connected to $R^6$.

8. The composition according to point 7, characterized in that the at least one odor modulator compound is selected from 2-acetylpyridine (CAS no. 1122-62-9), 2,5-dimethylpyrazine (CAS no. 123-32-0), 2,3,5-trimethylpyrazine (CAS no. 14667-55-1), 2-ethyl-3-methylpyrazine (CAS no. 15707-23-0), 2-acetylpyrazine (CAS no. 22047-25-2), 2-acetyl-3-methylpyrazine (CAS no. 23787-80-6), 2-isobutyl-3-methoxypyrazine (CAS no. 24683-00-9), 2,3-dimethylpyrazine (CAS no. 5910-89-4), 1-para-menthene-8-thiol (CAS no. 71159-90-5), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), 2-hydroxy-2-cyclohexen-1-one (CAS no. 10316-66-2), 2-(methylthio)phenol (CAS no. 1073-29-6), natural pyrazine mixture (CAS no. 84082-50-8), 2-methoxycinnamyl acetate (CAS no. 110823-66-0), 2,3,5,6-tetramethylpyrazine (CAS no. 1124-11-4), 2-hexylpyridine (CAS no. 1129-69-7), 2,6-dimethylthiophenol (CAS no. 118-72-9), 2-thiocresol (CAS no. 137-06-4), 2-ethylpyrazine (CAS no. 13925-00-3), 3-(2-methylpropyl)pyridine (CAS no. 14159-61-6), 2,3-diethylpyrazine (CAS no. 15707-24-1), 2-methyl-3-propylpyrazine (CAS no. 15986-80-8), 2,3-dihydro-5,6-dimethylpyrazine (CAS no. 15986-92-2), 2,3-diethyl-5-methylpyrazine (CAS no. 18138-04-0), 2-(3-phenylpropyl)pyridine (CAS no. 2110-18-1), 2-pentylpyridine (CAS no. 2294-76-0), 5-methyl-6,7-dihydrocyclopentapyrazine (CAS no. 23747-48-0), 3-methylcyclohexane-1,2-dione (CAS no. 300843-3), 2-acetyl-3-ethylpyrazine (CAS no. 32974-92-8), 3-acetylpyridine (CAS no. 350-03-8), 2-pyrazineethanethiol (CAS no. 35250-53-4), 2-phenylethanethiol (CAS no. 4410-99-5), 2-ethylthiophenol (CAS no. 4500-58-7), 3-ethylpyridine (CAS no. 536-78-7), 2-ethyl-3(5/6)-dimethylpyrazine (CAS no. 55031-15-7), 3,5,5-trimethylcyclohexane-1,2-dione (CAS no. 57696-89-6), 1,2-cyclohexanediol (CAS no. 57794-08-8), 2-propylpyridine (CAS no. 622-39-9), 1-phenylethanethiol (CAS no. 6263-65-6), 2-isobutylpyridine (CAS no. 6304-24-1), 4-allyl-2,6-dimethoxyphenol (CAS no. 6627-88-9), 2-methylthio-3(5/6)methylpyrazine (CAS no. 67952-65-2), benzyl methyl disulfide (CAS no. 699-10-5), 2-methylquinoxaline (CAS no. 7251-61-8), 2-acetyl-3,5 (6)-dimethylpyrazine (CAS no. 72797-17-2), ethyl 2-methoxybenzoate (CAS no. 7335-26-4), benzyl methyl sulfide (CAS no. 766-92-7), 2-methoxy-4-vinylphenol (CAS no. 7786-61-0), para-mentha-8-thioacetat-3-one (CAS no. 94293-57-9), maltol (CAS no. 118-71-8).

9. The composition according to point 7 or 8, characterized in that the at least one odor modulator compound is selected from 2-acetylpyridine (CAS no. 1122-62-9), 2,5-dimethylpyrazine (CAS no. 123-32-0), 2,3,5-trimethylpyrazine (CAS no. 1466755-1), 2-ethyl-3-methylpyrazine (CAS no. 15707-23-0), 2-acetylpyrazine (CAS no. 22047-25-2), 2-acetyl-3-methylpyrazine (CAS no. 23787-80-6), 2-isobutyl-3-methoxypyrazine (CAS no. 24683-00-9), 2,3-dimethylpyrazine (CAS no. 5910-89-4), 1-para-menthene-8-thiol (CAS no. 71159-90-5), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), maltol (CAS no. 118-71-8).

10. The composition according to point 1, comprising at least one odor modulator compound of general formula (III),

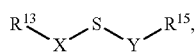

Formula (III)

where
X represents $CHR^{14}$, sulfur or a carbonyl group; and
Y represents $CHR^{16}$, sulfur, $CR^{16}R^{17}$ or a carbonyl group; and
$R^{13}$, $R^{14}$ and $R^{17}$ each represent, independently of one another, hydrogen or functional groups having 1 to 4 carbon atoms; and
$R^{15}$ and $R^{16}$ each represent, independently of one another, hydrogen or functional groups having 1 to 8 carbon atoms,
where
functional groups $R^{13}$ to $R^{17}$ are open-chain; and
one or more methyl groups, methylene groups, methine groups or quaternary carbon atoms of functional groups $R^{13}$ to $R^{17}$ may each, independently of one another, be substituted by heteroatoms.

11. The composition according to point 10, characterized in that
X represents $CHR^{14}$, sulfur or a carbonyl group; and
Y represents $CHR^{16}$, sulfur or a carbonyl group; and
$R^{13}$ and $R^{14}$ each represent, independently of one another, hydrogen or functional groups having 1 to 3 carbon atoms; and
$R^5$ and $R^{16}$ each represent, independently of one another, hydrogen or functional groups having 1 to 7 carbon atoms,
where
functional groups $R^{13}$ to $R^{16}$ are open-chain; and
one or more methyl groups, methylene groups, methine groups or quaternary carbon atoms of functional groups $R^{13}$ to $R^{16}$ may each, independently of one another, be substituted by heteroatoms.

12. The composition according to one of points 10 and 11, characterized in that the at least one odor modulator compound is selected from ethyl 3-methylthiopropionate (CAS no. 13327-56-5), methyl 3-methylthiopropionate (CAS no. 13532-18-8), 4-methylthio-4-methylpentan-2-one (CAS no. 23550-40-5), S-methyl butanethioate (CAS no. 2432-51-1), 3-methylthio-1-hexanol (CAS no. 51755-66-9), dibutyl sulfide (CAS no. 544-40-1), dipropyl sulfide (CAS no. 111-47-7), 1-(methylthio)-2-butanone (CAS no. 13678-58-5), 3-acetylthiohexylacetate (CAS no. 136954-25-1), 1-methylthio-1-propanone (CAS no. 14109-72-9), S-methyl thioacetate (CAS no. 1534-08-3), bis-(methylthio)methane (CAS no. 1618-26-4), 3-methylthiobutanal (CAS no. 16630-52-7), 3-(methylthio)propylacetate (CAS no. 16630-55-0), 3-(methylthio)propylbutyrate (CAS no. 16630-60-7), methyl(methylthio)acetate (CAS no. 16630-66-3), ethyl methyl disulfide (CAS no. 20333-39-5), diallyl trisulfide (CAS no. 2050-87-5), 4-methylthiobutanol (CAS no. 20582-85-8), diallyl disulfide (CAS no. 2179-57-9), allyl methyl sulfide (CAS no. 2179-58-0), allyl propyl disulfide (CAS no. 2179-59-1), 2,3-dithiahexane (CAS no. 2179-60-4), 2-methylthioacetaldehyde (CAS no. 23328-62-3), ethyl propyl disulfide (CAS no. 30453-31-7), 3-methylthiopropanal (CAS no. 3268-49-3), 4-(methylthio)-2-butanone (CAS no. 34047-39-7), 3-methylthiohexanal (CAS no. 38433-74-8), 3-methylthiopropylamine (CAS no. 4104-45-4), S-methyl-2-methylbutanethioate (CAS no. 42075-45-6), diisopropyl disulfide (CAS no. 4253-89-8), ethyl 2-(methylthio)acetate (CAS no. 4455-13-4), ethyl 2-methyl-2-methylthiopropionate (CAS no. 49773-24-2), 2-(ethylthio)-1-propanol (CAS no. 72311-96-7), 3-methylthiopropanol (CAS no. 505-10-2), 3-methylthiopropylisothiocyanate (CAS no. 505-79-3), methyl 2-(methylthio)butyrate (CAS no. 51534-66-8), 3-methylthio-hex-1-ylacetate (CAS no. 51755-85-2), 2-(methylthio)ethanol (CAS no. 5271-38-5), methyl 4-methylthiobutyrate (CAS no. 53053-51-3), dipropyl trisulfide (CAS no. 6028-61-1), S-methyl-4-methyl pentanethioate (CAS no. 61122-71-2), dimethyl disulfide (CAS no. 624-92-0), ethyl thioacetate (CAS no. 625-60-5), n-butyl methyl sulfide (CAS no. 628-29-5), dipropyl disulfide (CAS no. 629-19-6), 2,4,6-trithiaheptane (CAS no. 6540-86-9), amyl methyl disulfide (CAS no. 72437-68-4), methyl thiomethyl hexanoate (CAS no. 74758-91-1), methyl thiomethyl butyrate (CAS no. 74758-93-3), isoamyl 3-methylthiopropionate (CAS no. 93762-35-7), 1-(methylthio)pentan-3-one (CAS no. 66735-69-1), 3-(methylthio)propyl mercaptoacetate (CAS no. 852997-30-9), methyl isobutanethioate (CAS no. 42075-42-3).

13. The composition according to one of points 10 to 12, characterized in that the at least one odor modulator compound is selected from ethyl 3-methylthiopropionate (CAS no. 13327-56-5), methyl 3-methylthiopropionate (CAS no. 13532-18-8), 4-methylthio-4-methylpentan-2-one (CAS no. 23550-40-5), S-methyl butanethioate (CAS no. 2432-51-1), 3-methylthio-1-hexanol (CAS no. 51755-66-9), dibutyl sulfide (CAS no. 544-40-1), 1-(methylthio)pentan-3-one (CAS no. 66735-69-1), 3-(methylthio)propyl mercaptoacetate (CAS no. 852997-30-9), methyl isobutanethioate (CAS no. 42075-42-3).

14. The composition according to point 1, comprising at least one odor modulator compound of general formula (IV),

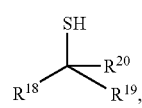

Formula (IV)

where
$R^{18}$ and $R^{19}$ each represent, independently of one another, hydrogen or a functional group having 1 to 3 carbon atoms; and
$R^{20}$ represents a functional group having 3 to 10 carbon atoms,
where
functional groups $R^{18}$ to $R^{20}$ are open-chain; and
one or more methyl groups, methylene groups, methine groups or quaternary carbon atoms of functional groups $R^{18}$ to $R^{20}$ may each, independently of one another, be substituted by heteroatoms, with the proviso that the at least one odor modulator compound of general formula (IV) is not 3-mercapto-1-hexenol (CAS no. unknown), 3-mercapto-3-methyl-1-hexanol (CAS no. 307964-23-4), 3-mercapto-2-methylbutan-1-ol (CAS no. 227456-33-9), 3-mercaptopentan-1-ol (CAS no. 548740-99-4) or 3-mercaptohexan-1-ol (CAS no. 51755-83-0).

15. The composition according to point 14, characterized in that
$R^{18}$ and $R^{19}$ each represent, independently of one another, hydrogen or a methyl group, where it is preferred for $R^{18}$ to represent a methyl group and $R^{19}$ to represent hydrogen; and
$R^{20}$ represents a functional group having 3 to 10 carbon atoms, preferably a functional group having 3 to 8 carbon atoms,
where
at least one methyl group, methylene group, methine group or quaternary carbon atom of functional group $R^{20}$ is substituted by a heteroatom, preferably oxygen.

16. The composition according to point 14 or 15, characterized in that the at least one odor modulator compound is selected from ethyl 2-mercaptopropionate (CAS no. 19788-49-9), 2-mercaptopropionic acid (CAS no. 79-42-5), 1-pentanethiol (CAS no. 110-66-7), 1,6-hexanedithiol (CAS no. 1191-43-1), 3-thiohexylacetate (CAS no. 136954-20-6), 3-mercaptohexylbutyrate (CAS no. 136954-21-7), 3-mercaptohexylhexanoate (CAS no. 136954-22-8), 2-methylbutane-1-thiol (CAS no. 1878-18-8), 4-methyl-4-mercaptopentan-2-one (CAS no. 19872-52-7), 3-methyl-2-butanethiole (CAS no. 2084-18-6), 2-pentanethiol (CAS no. 2084-19-7), thiogeraniol (CAS no. 39067-80-6), 3-mercapto-2-butanone (CAS no. 40789-98-8), 3-mercapto-2-pentanone (CAS no. 67633-97-0), allyl mercaptan (CAS no. 870-23-5), 1,5-pentanedithiol (CAS no. 928-98-3), propyl-2-mercaptopropionate (CAS no. 19788-50-2), 2,2-(dithiomethylene)difuran (CAS no. 4437-20-1), 4-methoxy-2-methylbutanethiol (CAS no. 301977-9), grapefruit mercaptan (CAS no. 71159-90-5).

17. The composition according to one of points 14 to 16, characterized in that the at least one odor modulator compound is selected from ethyl 2-mercaptopropionate (CAS no. 19788-49-9), 2-mercaptopropionic acid (CAS no. 79-42-5), propyl-2-mercaptopropionate (CAS no. 19788-50-2), 2,2-(dithiomethylene)difuran (CAS no. 4437-20-1), 4-methoxy-2-methylbutanethiol (CAS no. 301-977-9), grapefruit mercaptan (CAS no. 71159-90-5).

18. The composition according to one of points 1 to 17, characterized in that the composition according to the invention contains one to six odor modulator compounds, preferably one to five odor modulator compounds, more preferably one to four odor modulator compounds, and most preferably one to three odor modulator compounds.

19. The composition according to one of points 1 to 18, characterized in that the at least one odor modulator compound is used, based on the total of all the odorants contained in the perfume composition, in a weight ratio of at most 1:9, preferably at most 1:49, more preferably at most 1:99, and most preferably at most 1:299.

20. The composition according to one of points 1 to 19, characterized in that the at least one odor modulator compound is contained in an amount of from 1.5 wt. % to 0.000001 wt. %, preferably from 1.0 wt. % to 0.000001 wt. %, more preferably from 0.5 wt. % to 0.000001 wt. %, most preferably from 0.25 wt. % to 0.000001 wt. %, with wt. % based in each case on the total of all the odorants contained in the perfume composition.

21. The composition according to one of points 1 to 20, characterized in that the at least one odor modulator compound contains one to five heteroatoms, preferably one to four heteroatoms, and most preferably one to three heteroatoms, selected from the group of N, O or S.

22. The composition according to one of points 1 to 21, characterized in that the at least one odor modulator compound has a molecular weight of lower than 225 g mol$^{-1}$, and more preferably lower than 200 g mol$^{-1}$.

23. The composition according to one of points 1 to 22, characterized in that the at least one odor modulator compound has a boiling point of lower than 250° C., preferably lower than 225° C., more preferably 200° C., and most preferably lower than 175° C.

24. The composition according to one of points 1 to 23, characterized in that an efficiency factor according to the formula in point 1 of at least 1.5, more preferably at least 1.75, is achieved on account of the at least one odor modulator compound.

25. The composition according to one of points 1 to 24, characterized in that the at least one odor modulator compound has an odor detection threshold of lower than 100 ppb, preferably lower than 75 ppb, more preferably lower than 50 ppb, even more preferably lower than 35 ppb, even more preferably lower than 10 ppb, most preferably lower than 1 ppb.

26. The composition according to one of points 1 to 25, characterized in that the at least one odor modulator compound is selected from pyrroles, pyridines, pyrazines, thiols, sulfides, thiazoles, thiophenes, furans, oxazolines, oxazoles and/or oxathiones.

27. The composition according to one of points 1 to 26, characterized in that the microcapsules are core/shell microcapsules.

28. The composition according to one of points 1 to 27, characterized in that the microcapsules have a semipermeable shell, and the capsule core comprises at least 50 wt. % of the at least one odor modulator compound, and the microcapsules and the capsule core are preferably free of odorants.

29. The composition according to one of points 1 to 28, characterized in that the microcapsules have an impermeable shell, and the core contains at least 70 wt. %, preferably at least 80 wt. %, and most preferably at least 85 wt. %, of the at least one odorant.

30. The composition according to one of points 1 to 29, characterized in that the shell of the microcapsules comprises a wall material selected from melamine/formaldehyde polymer, melamine/urea polymer, melamine/urea/formaldehyde polymer, polyacrylate polymer or polyacrylate copolymer.

31. The composition according to one of points 1 to 30, characterized in that the microcapsules have a surface coating, comprising a cationic polymer, over the whole or part of the surface of said microcapsules.

32. The perfume composition according to one of points 1 to 31, characterized in that the composition according to the invention contains microcapsules according to point 28 and point 29.

33. The perfume composition according to one of points 1 to 32, characterized in that the perfume composition contains two or more different types of microcapsules according to point 28 or 29.

34. The composition of one of points 1 to 33, characterized in that the microcapsules have an average diameter $X_{50.3}$ (volume average) of from 0.1 to 200 μm, preferably from 1 to 100 μm, more preferably from 5 to 80 μm, particularly preferably from 10 to 50 jam, and in particular from 15 to 40 μm.

35. The composition according to one of points 1 to 34, characterized in that the microcapsules are contained in an amount of from 0.0005 to 0.15 wt. %, preferably from 0.001 to 0.1 wt. %, very particularly preferably from 0.01 to 0.1 wt. %.

36. The composition according to one of points 1 to 35, characterized in that additionally at least one surfactant, selected from anionic, cationic or nonionic surfactants, is contained.

37. The composition according to one of points 1 to 36, characterized in that additionally at least one surfactant, in particular at least one anionic sulfonate-type or sulfate-type surfactant or a mixture thereof, is contained.

38. The composition according to one of points 1 to 37, characterized in that at least one cationic surfactant is contained, which can be obtained by reacting
(i) a mixture of at least one dicarboxylic acid of formula (K-I)

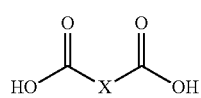

(K-I)

where X represents a saturated or unsaturated hydrocarbon functional group having 1 to 8 carbon atoms, and
of at least one monocarboxylic acid of formula (K-II)

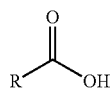

(K-II)

where R represents a saturated or unsaturated hydrocarbon functional group having 5 to 21 carbon atoms, with
(ii) at least one tertiary amine of formula (K-III)

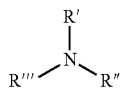

(K-III)

where R', R" and R'" represent, independently of one another, a ($C_2$ to $C_6$) hydroxyalkyl group, in particular 2-hydroxyethyl,
and by subsequently reacting the resulting product with
(iii) at least one quaternization agent for quaternizing at least one amino group contained in the reaction product.

39. The composition according to one of points 1 to 38, characterized in that additionally at least one thickener is contained.

40. The composition according to point 39, characterized in that, as a thickener, at least one polymeric thickener is additionally contained, which is obtained by copolymerizing at least the following monomers: (i) acrylic acid or methacrylic acid, (ii) at least one ester of acrylic acid with a $C_{1-4}$ alkanol and/or at least one ester of methacrylic acid with a $C_{1-4}$ alkanol, (iii) optionally at least one monomer of formula (M1)

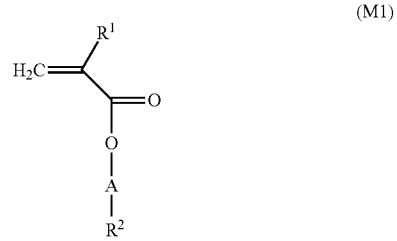

where
$R^1$ represents a hydrogen atom or a methyl group,
$R^2$ represents a ($C_8$-$C_{30}$) alkyl group,
A represents a group *—$(CH_2CH_2O)_x$—* where X represents an integer from 5 to 35, a group *—$(CH_2CHMeO)_y$—* where y represents an integer from 5 to 35, or a group *—$(CH_2CH_2O)_x$—$(CH_2CHMeO)_y$—* where the sum x+y represents an integer from 5 to 35 and x and y are greater than zero.

41. The composition according to point 40, characterized in that at least one polymeric thickener selected from polysaccharide, in particular from starch, dextrin, carboxymethyl starch, cellulose, carboxymethyl cellulose, hydroxyethyl cellulose, xanthan gum, carrageenan, guar gum and gum arabic or mixtures thereof, is contained as a further thickener.

42. The composition according to one of points 1 to 41, characterized in that additionally at least one inorganic salt is contained, preferably in an amount of from 0.1 to 1.5 wt. %, in particular from 0.2 to 1.2 wt. %, very particularly preferably from 0.3 to 1.0 wt. %.

43. The composition as a suspension of optical effect solids, selected from pearlescing pigments, speckles, dye pigments and mixtures thereof, in a composition according to one of points 1 to 42 as a continuous phase.

44. A method for fragrancing a substrate (in particular textiles), in which method the composition according to one of points 1 to 43 is brought into contact with the substrate (in particular textiles), optionally as a dilution.

EXAMPLES

Perfume Oils

Table 1 shows perfume oils 1 and 2, perfume oil 2 comprising four odor modulator compounds (OMC) in a total amount of 0.2 wt. %, with wt. % based on the overall perfume oil, and perfume oil 1 comprising, instead of the odor modulator compounds, 0.2 wt. % of the solvent dipropylene glycol.

TABLE 1

| Composition of perfume oils 1 and 2. | | |
|---|---|---|
| Odorant/OMC/Solvent | Perfume Oil 1 (wt. %) | Perfume Oil 2 (wt. %) |
| Rose oxide | 3.8 | 3.8 |
| Aldehyde C11 | 11 | 11 |
| Dihydro floriffone | 15 | 15 |
| alpha-Ionone | 30 | 30 |
| Phenylethyl formate | 20 | 20 |
| Phenyl acetaldehyde | 20 | 20 |
| Dipropylene glycol | 0.2 | — |
| 3-Methylthio-1-hexanol (CAS no. 51755-66-9) | — | 0.1 |
| Dibutyl sulfide (CAS no. 544-40-1) | — | 0.06 |

TABLE 1-continued

Composition of perfume oils 1 and 2.

| Odorant/OMC/Solvent | Perfume Oil 1 (wt. %) | Perfume Oil 2 (wt. %) |
|---|---|---|
| 4-Methylthio-4-methylpentan-2-one (CAS no. 23550-40-5) | — | 0.02 |
| 1-para-Menthene-8-thiol (CAS no. 71159-90-5) | — | 0.02 |
| Total Amount | 100 | 100 |

The perfume oils from Table 1 were used in the following perfume compositions PZ-1 to PZ-4 in Table 2.

Perfume Compositions

The perfume compositions PZ-1 and PZ-2 contained in Table 2 consisted substantially of perfume oils 1 and 2, respectively, the two perfume oils being non-encapsulated. The perfume compositions PZ-3 and PZ-4 consisted substantially of microcapsules (melamine/formaldehyde) comprising perfume oils 1 and 2, respectively.

TABLE 2

Perfume compositions PZ-1 to PZ-4. PZ-4 corresponds to a perfume composition according to the invention.

| | Perfume Compositions | | | |
|---|---|---|---|---|
| | PZ-1 | PZ-2 | PZ-3 | PZ-4 |
| Perfume Oil | 1 | 2 | 1 | 2 |
| Microcapsules | no | no | yes | yes |
| OMC | no | yes | no | yes |

Liquid Washing Agent

The following liquid washing agents were produced by mixing the components. The perfume capsules were incorporated into the liquid washing agent as a water-comprising suspension. The transmission of light of a wavelength of 500 nm through a sample of each of compositions E1 and V1 was determined at 20° C.

| Raw material | E1 (wt. %) | V1 (wt. %) |
|---|---|---|
| $C_{10-13}$ alkyl benzene sulfonic acid | 3.5 | 3.5 |
| Fatty alcohol ether sulfate having 2 moles of ethylene oxide | 3.9 | 3.9 |
| $C_{13-15}$ alkyl ether having 7 moles of ethylene oxide | 4.3 | 4.3 |
| Builders (citric acid and phosphonates) | 0.55 | 0.55 |
| NaCl | 0.8 | 0.8 |
| $C_{12-18}$ coconut fatty acid | 0.6 | 0.6 |
| Glycerol | 0.6 | 0.6 |
| Polymeric associative acrylate thickener | 0.4 | 0.4 |
| Enzymes (protease, amylase, cellulase, lipase, mannanase) | 0.4 | 0.4 |
| Boric acid | 0.6 | 0.6 |
| Microcapsule PZ-3 | — | 0.4 |
| Microcapsule PZ-4 | 0.05 | — |
| Perfume oil P1 | 0.2 | 0.2 |
| Further additives (preservative, defoamer, optical brightener, dye) | 0.49 | 0.49 |
| Water | Balance | Balance |
| Transmission (500 nm) | 60.7% | 12.4% |

Textiles were washed using composition E1 according to the invention and comparative composition V1.

Washing Conditions

Washing machine: Miele Softtronic W1734
Programme: main washing cycle at 40° C.
Water hardness: 16° dH
Spin speed: 1,200 rpm
Amount of textiles: 3 kg (mixed textiles)
Test textiles: cotton toweling 30×30 cm Drying Conditions Temperature: 20° C.
Humidity: 60% rh.

The fragrance profile, the intensity and the durability of the fragrance on the textile was compared by experts. After washing and drying, the textiles had the same fragrance profile having the same durable intensity.

Despite the addition of microcapsules, liquid washing agent E1 was demonstrably far more transparent than comparative formulation V1.

What is claimed is:

1. A liquid, transparent composition for textile treatment, comprising
    a) at least one odorant
      and
    b) from 0.00001 to 0.2 wt. % microcapsules, comprising at least one odor modulator compound, wherein each individual modulator compound
      i) is contained, based on the total of all the odorants contained in the composition, in an amount of from 2 wt. % to 0.000001 wt. %, and
      ii) contains at least one heteroatom, wherein the at least one heteroatom is selected from N, O, S, Si, Se, F, Cl, Br or I, and
      iii) has a molecular weight of lower than 250 g mol$^{-1}$, and
    wherein the composition has an efficiency factor of at least 1.15 on account of the at least one odor modulator compound, wherein the efficiency factor is calculated according to the following formula:

$$E = \frac{P_{GMV}}{P+1} \geq 1.15$$

where E=efficiency factor and P=number of persons trained in odors that deemed the composition having an odor modulator compound ($P_{GMV}$) or not having an odor modulator compound (P) to be more intense, wherein the sum of $P_{GMV}$ and P is at least 34, and wherein the composition has a turbidity of less than 60 NTU at 20 deg. C.

2. The liquid composition according to claim 1, wherein the at least one odor modulator compound is selected from 2-acetylpyridine (CAS no. 1122-62-9), 2,5-dimethylpyrazine (CAS no. 123-32-0), ethyl 3-methylthiopropionate (CAS no. 13327-56-5), methyl 3-methylthiopropionate (CAS no. 13532-18-8), 2,3,5-trimethylpyrazine (CAS no. 14667-55-1), 2-ethyl-4-methylthiazole (CAS no. 15679-12-6), 2-isopropyl-4-methylthiazole (CAS no. 15679-13-7), 2-ethyl-3-methylpyrazine (CAS no. 15707-23-0), 2-isobutylthiazole (CAS no. 18640-74-9), ethyl 2-mercaptopropionate (CAS no. 19788-49-9), 2-acetylpyrazine (CAS no. 22047-25-2), 4-methylthio-4-methylpentan-2-one (CAS no. 23550-40-5), 2-acetyl-3-methylpyrazine (CAS no. 23787-80-6), 2-acetylthiazole (CAS no. 24295-03-2), S-methyl butanethioate (CAS no. 2432-51-1), 2-isobutyl-3- methoxypyrazine (CAS no. 24683-00-9), 2,2'-(dithiodimethylene)difuran (CAS no. 4437-20-1), 3-methylthio-1-hexanol (CAS no. 51755-66-9), 3-mercapto-1-hexanol (CAS no. 51755-83-0), dibutyl sulfide (CAS no. 544-40-1), 2,3-dimethylpyrazine (CAS no. 5910-89-4), 1-para-menthene-8-thiol (CAS no. 71159-90-5), 2-mercaptopropionic acid (CAS no. 79-42-5), 2,2,4,4,6,6-hexamethyl-1,3,5-trithiane (CAS no. 828-26-2), furfuryl mercaptan (CAS no. 98-02-2), menthofuran (CAS no. 494-90-6), homofuranol (CAS no. 27538-09-6), furaneol (CAS no. 3658-77-3), 1-(2-benzofuranyl)ethanone (CAS no. 1646-26-0), nerolione (CAS no. 23911-56-0), methyl corylone (CAS no. 13494-06-9), sotolone (CAS no. 28664-35-9), furaneol methyl ether (CAS no. 4077-47-8), emoxyfurone (CAS no. 698-10-2), 2-ethyl-3,5-dimethylpyrazine (CAS no. 27043-05-6), 2-methyl-3-(methylthio)pyrazine (CAS no. 2882-20-4), 2-methoxy-3-methylpyrazine (CAS no. 2847-30-5), 2-methoxy-6-methylpyrazine (CAS no. 2882-21-5), 2-methoxy-3-isopropylpyrazine (CAS no. 25773-40-4), 4-(4,8-dimethyl-3,7nonadienyl)pyridine (CAS no. 38462-23-6), 5-hexyl-2-methylpyridine (CAS no. 710-40-7), thiomenthone (CAS no. 38462-22-5), thiocineol (CAS no. 68398-18-5), sulfurol (CAS no. 137-00-8), benzothiazole (CAS no. 95-16-9), 4,5-dihydro-3(2H)thiophenone (CAS no. 1003-04-9), 2-hydroxy-2-cyclohexen-1-one (CAS no. 10316-66-2), 3-acetyl-2,5-dimethylfuran (CAS no. 10599-70-9), 2-propionylpyrrole (CAS no. 1073-26-3), 2-(methylthio)phenol (CAS no. 1073-29-6), methyl 2-furfurylthioacetate (CAS no. 108499-33-8), furfurylideneacetone (CAS no. 108811-61-6), natural pyrazine mixture (CAS no. 84082-50-8), 1-pentanethiol (CAS no. 110-66-7), 2-methoxycinnamyl acetate (CAS no. 110823-66-0), dipropyl sulfide (CAS no. 111-47-7), 2,3,5,6-tetramethylpyrazine (CAS no. 1124-11-4), 2-hexylpyridine (CAS no. 1129-69-7), 4-butyroxy-2,5-dimethyl-3(2H)-furanone (CAS no. 114099-96-6), 2,6-dimethylthiophenol (CAS no. 118-72-9), 2-methylheptanoic acid (CAS no. 1188-02-9), 1,6-hexanedithiol (CAS no. 1191-43-1), 2-acetylfuran (CAS no. 1192-62-7), 2-acetyl-5-methylfuran (CAS no. 1193-79-9), 2,4,5-trimethylthiazole (CAS no. 13623-11-5), 1-(methylthio)-2-butanone (CAS no. 13678-58-5), 2-methyl-5-thiomethylfuran (CAS no. 13678-59-6), furfuryl thioacetate (CAS no. 13678-68-7), 3-thiohexylacetate (CAS no. 136954-20-6), 3-mercaptohexylbutyrate (CAS no. 136954-21-7), 3-mercaptohexylhexanoate (CAS no. 136954-22-8), 3-acetylthiohexylacetate (CAS no. 136954-25-1), 2-thiocresol (CAS no. 137-06-4), 2-ethylpyrazine (CAS no. 13925-00-3), 1-methylthio-2-propanone (CAS no. 14109-72-9), 3-(2-methylpropyl)pyridine (CAS no. 14159-61-6), furfuryl methyl sulfide (CAS no. 1438-91-1), 1-(2-furanylmethyl)-1H-pyrrole (CAS no. 1438-94-4), 2-butylthiophene (CAS no. 1455-20-5), S-methyl thioacetate (CAS no. 1534-08-3), 2,3-diethylpyrazine (CAS no. 15707-24-1), 2-methyl-3-propylpyrazine (CAS no. 15986-80-8), 2,3-dihydro-5,6-dimethylpyrazine (CAS no. 15986-92-2), bis-(methylthio)methane (CAS no. 1618-26-4), 3-methylthiobutanal (CAS no. 16630-52-7), 3-(methylthio)propylacetate (CAS no. 16630-55-0), 3-(methylthio)propylbutyrate (CAS no. 16630-60-7), methyl (methylthio)acetate (CAS no. 16630-66-3), 4-methyl-5-vinylthiazole (CAS no. 1759-28-0), 2,3-diethyl-5-methylpyrazine (CAS no. 18138-04-0), 2-(1-methylpropyl)thiazole (CAS no. 18277-27-5), 2-methylbutane-1-thiol (CAS no. 1878-18-8), 2-hexylthiophene (CAS no. 18794-77-9), furfuryl isopropyl sulfide (CAS no. 1883-78-9), 4-methyl-4-mercaptopentan-2-one (CAS no. 1987252-7), ethyl methyl disulfide (CAS no. 20333-39-5), diallyl trisulfide (CAS no. 2050-87-5), 4-methylthiobutanol (CAS no. 20582-85-8), 2,4,5-trimethyloxazole (CAS no. 20662-84-4), 3-methyl-2-butanethiole (CAS no. 2084-18-6), 2-pentanethiol (CAS no. 2084-19-7), 2-(3-phenylpropyl)pyridine (CAS no. 2110-18-1), diallyl disulfide (CAS no. 2179-57-9), allyl methyl sulfide (CAS no. 2179-58-0), allyl propyl disulfide (CAS no. 2179-59-1), 2,3-dithiahexane (CAS no. 2179-60-4), 2,4,5-trimethyl-3-oxazoline (CAS no. 22694-96-8), 2-pentylpyridine (CAS no. 2294-76-0), 2-methylthioacetaldehyde (CAS no. 23328-62-3), 2-methyl-2-thiazoline (CAS no. 2346-00-1), 3,5-dimethyl-1,2,4-trithiolane (CAS no. 23654-92-4), 5-methyl-6,7-dihydrocyclopentapyrazine (CAS no. 23747-48-0), 2-methylthiazolidine (CAS no. 24050-16-6), 2-methyltetrahydrofuran-3-thioacetate (CAS no. 252736-41-7), 2-methyl-3-furanthiol (CAS no. 28588-74-1), bis-(2-methyl-3-tetrahydrofuran)disulfide (CAS no. 28588-75-2), 3-methylcyclohexane-1,2-dione (CAS no. 3008-43-3), ethyl propyl disulfide (CAS no. 30453-31-7), 3(5-methyl-2-furyl)butanal (CAS no. 31704-80-0), 2-methyltetrahydrofuran-3-one (CAS no. 3188-00-9), 2-pentanoylfuran (CAS no. 3194-17-0), 2-ethylfuran (CAS no. 3208-16-0), 3-methylthiopropanal (CAS no. 3268-49-3), 2-acetyl-3-ethylpyrazine (CAS no. 32974-92-8), 4-(methylthio)-2-butanone (CAS no. 34047-39-7), 3-acetylpyridine (CAS no. 350-03-8), 2-pyrazineethanethiol (CAS no. 35250-53-4), 4,5-dimethylthiazole (CAS no. 3581-91-7), 2-pentylfuran (CAS no. 3777-69-3), 2-heptylfuran (CAS no. 3777-71-7), 5-acetyl-2,4-dimethylthiazole (CAS no. 38205-60-6), 3-methylthiohexanal (CAS no. 38433-74-8), thiogeraniol (CAS no. 39067-80-6), 2-ethyl-5-methylthiophene (CAS no. 40323-88-4), 3-mercapto-2-butanone (CAS no. 40789-98-8), 3-methylthiopropylamine (CAS no. 4104-45-4), 4-acetoxy-2,5-dimethyl-3(2H)-furanone (CAS no. 4166-20-5), S-methyl-2-methylbutanethioate (CAS no. 42075-45-6), 2-propylfuran (CAS no. 4229-91-8), diisopropyl disulfide (CAS no. 4253-89-8), 2-propionylthiazole (CAS no. 43039-98-1), 2-phenylethanethiol (CAS no. 4410-99-5), ethyl 2-(methylthio)acetate (CAS no. 4455-13-4), 2-butylfuran (CAS no. 4466-24-4), 2-ethylthiophenol (CAS no. 4500-58-7), 2-pentylthiophene (CAS no. 4861-58-9), ethyl 2-methyl-2-methylthiopropionate (CAS no. 49773-24-2), 2-(ethylthio)-1-propanol (CAS no. 72311-96-7), 3-methylthiopropanol (CAS no. 505-10-2), 3-methylthiopropylisothiocyanate (CAS no. 505-79-3), thioacetic acid (CAS no. 507-09-5), methyl 2-(methylthio)butyrate (CAS no. 51534-66-8), 3-methylthio-hex-1-ylacetate (CAS no. 51755-85-2), 2-(methylthio)ethanol (CAS no. 5271-38-5), methyl 4-methylthiobutyrate (CAS no. 53053-51-3), 2-isobutyl-4,5-dimethylthiazole (CAS no. 5349832-1), 3-ethylpyridine (CAS no. 536-78-7), 2-ethyl-4,5-dimethyloxazole (CAS no. 53833-30-0), 2,4-dimethylthiazole (CAS no. 541-58-2), 2-butyl-5-ethylthiophene (CAS no. 54411-06-2), 2,4,6-triethyldihydro-1,3,5-dithiazine (CAS no. 54717-17-8), 3-mercapto-2-butanol (CAS no. 54812-86-1), 2-ethyl-3(5/6)-dimethylpyrazine (CAS no. 55031-15-7), 2-methyl-1,3-dithiolane (CAS no. 561651-3), 2-methyltetrahydrofuran-3-thiol (CAS no. 57124-87-5), 3,5,5-trimethylcyclohexane-1,2-dione (CAS no. 57696-89-6), 1,2-cyclohexanediol (CAS no. 57794-08-8), furfuryl thiopropionate (CAS no. 59020-85-8), furfuryl thioformate (CAS no. 59020-90-5), dipropyl trisulfide (CAS no. 6028-61-1), S-methyl-4-methyl pentanethioate (CAS no. 61122-71-2), 5-methylfurfural (CAS no. 620-02-0), 2-propylpyridine (CAS no. 622-39-9), furfuryl acetate (CAS no. 623-17-6), 3-(2-furyl)acrolein (CAS no. 623-30-3), dimethyl disulfide (CAS no. 624-92-0), ethyl thioacetate (CAS no. 625-60-5), 2-thienylmercaptan (CAS no. 6258-63-5), 1-phenylethanethiol (CAS no. 6263-65-6), n-butyl methyl sulfide (CAS no. 628-29-5), dipropyl disulfide (CAS no. 629-19-6), 2-isobutylpyridine (CAS no. 6304-24-1), 2,5-dimethylthiophene (CAS no. 638-02-8), 2,4,6-trithiaheptane (CAS no. 6540-86-9), 4-methyl-5-thiazolethanolacetate (CAS no. 656-53-1), 2-(sec-butyl)-4,5-dimethyl-3-thiazoline (CAS no. 65894-82-8), 2-isobutyl-4,5-dimethyl-3-thiazoline (CAS no. 65894-83-9), 4-allyl-2,6-dimethoxyphenol (CAS no. 6627-88-9), 3-mercapto-2-pentanone (CAS no. 67633-97-0), 2-methyl-4-propyl-1,3-oxathiane (CAS no. 59323-76-1), 2-methylthio-3(5/6) methylpyrazine (CAS no. 67952-65-2), 4-methylthiazole (CAS no. 693-95-8), 2-furyl-2-propanone (CAS no. 6975-60-6), benzyl methyl disulfide (CAS no. 699-10-5), amyl methyl disulfide (CAS no. 72437-68-4), 2-methylquinoxaline (CAS no. 7251-61-8), 2-acetyl-3,5(6)-dimethylpyrazine (CAS no. 72797-17-2), diallyl polysulfide (CAS no. 72869-75-1), ethyl 2-methoxybenzoate (CAS no. 7335-26-4), methyl thiomethyl hexanoate (CAS no. 74758-91-1), methyl thiomethyl butyrate (CAS no. 74758-93-3), methyl mercaptan (CAS no. 74-93-1), benzyl methyl sulfide (CAS no. 766-92-7), 2-ethyl-4,5-dimethylthiazoline (CAS no. 76788-46-0), 2-methoxy-4-vinylphenol (CAS no. 7786-61-0), allyl mercaptan (CAS no. 870-23-5), 2-methyl-3-(2-furyl)prop-2-enal (CAS no. 874-66-8), 2-octylthiophene (CAS no. 880-36-4), 1,5-pentanedithiol (CAS no. 928-98-3), isoamyl 3-methylthiopropionate (CAS no. 93762-35-7), ethyl 3-(furfurylthiol)propionate (CAS no. 94278-27-0), para-mentha-8-thioacetat-3-one (CAS no. 94293-57-9), furfuryl alcohol (CAS no. 98-00-0), 3-acetyl-2,5-dimethylthiophene (CAS no. 2530-10-1), ethyl 2-methylbutyrate (CAS no. 7452-79-1), decenal-4-trans (CAS no. 65405-70-1).

3. The liquid composition according to claim 1, wherein the at least one odor modulator comprises a compound of general formula (II),

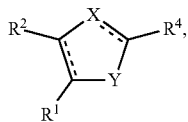

Formula (II)

where
X represents nitrogen, sulfur or $CR^3$; and
Y represents oxygen, sulfur or $NR^5$; and
$R^1$, $R^2$ and $R^5$ each represent, independently of one another, hydrogen or functional groups having 1 to 6 carbon atoms; and
$R^3$ and $R^4$ each represent, independently of one another, hydrogen or functional groups having 1 to 9 carbon atoms,
where
the ring of formula (II) may contain, at the positions linked by dashed lines, each independently of one another, double bonds, with the proviso that the at least one odor modulator compound, if X represents nitrogen, contains a double bond between X and the carbon atom of the ring of formula (II) that is linked to $R^4$; and
the carbon atoms of the ring of formula (II) that are linked to $R^1$ and $R^2$ may together be part of an annulated five-member or six-member ring, where functional groups $R^1$ and $R^2$ are each, independently of one another, an integral part of the annulated ring either completely or in part; and
one or more methyl groups, methylene groups, methine groups or quaternary carbon atoms of functional groups $R^1$ to $R^5$ may each, independently of one another, be substituted by heteroatoms.

4. The liquid composition according to claim 1, comprising at least one odor modulator compound of general formula (III),

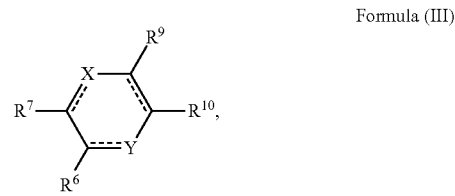

Formula (III)

where
X represents nitrogen or $CR^8$; and
Y represents nitrogen, $CR^{11}$ or $CR^{11}R^{12}$, and
$R^6$ and $R^8$ each represent, independently of one another, hydrogen or functional groups having 1 to 10 carbon atoms; and
$R^7$ and $R^9$ to $R^{12}$ each represent, independently of one another, hydrogen or functional groups having 1 to 4 carbon atoms,
where
the ring of formula (III) may contain, at the positions connected by dashed lines, each independently of one another, double bonds, with the proviso that the at least one odor modulator compound, if X or Y represents nitrogen, contains a double bond between X and the carbon atom of the ring of formula (III) that is linked to $R^7$, or between Y and the carbon atom of the ring of formula (III) that is linked to $R^6$, respectively; and
the carbon atoms of the ring of formula (III) that are linked to $R^6$ and $R^7$ may together be part of an annulated five-member or six-member ring, where functional groups $R^6$ and $R^7$ are each, independently of one another, an integral part of the annulated ring either completely or in part; and
one or more methyl groups, methylene groups, methine groups or quaternary carbon atoms of functional groups $R^6$ to $R^{12}$ may each, independently of one another, be substituted by heteroatoms; and
if Y represents $CR^{11}R^{12}$, there is no double bond between Y and the carbon atom of the ring that is connected to $R^6$.

5. The liquid composition according to claim 1, comprising at least one odor modulator compound of general formula (IV),

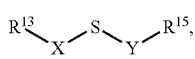

Formula (IV)

where
X represents $CHR^{14}$, sulfur or a carbonyl group; and
Y represents $CHR^{16}$, sulfur, $CR^{16}R^{17}$ or a carbonyl group; and
$R^{13}$, $R^{14}$ and $R^{17}$ each represent, independently of one another, hydrogen or functional groups having 1 to 4 carbon atoms; and
$R^{15}$ and $R^{16}$ each represent, independently of one another, hydrogen or functional groups having 1 to 8 carbon atoms, where
- functional groups $R^{13}$ to $R^{17}$ are open-chain; and
- one or more methyl groups, methylene groups, methine groups or quaternary carbon atoms of functional groups $R^{13}$ to $R^{17}$ may each, independently of one another, be substituted by heteroatoms.

6. The liquid composition according to claim 1, comprising at least one odor modulator compound of general formula (V),

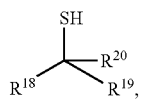

Formula (V)

where
- $R^{18}$ and $R^{19}$ each represent, independently of one another, hydrogen or a functional group having 1 to 3 carbon atoms; and
- $R^{20}$ represents a functional group having 3 to 10 carbon atoms, where
- functional groups $R^{18}$ to $R^{20}$ are open-chain; and
- one or more methyl groups, methylene groups, methine groups or quaternary carbon atoms of functional groups $R^{18}$ to $R^{20}$ may each, independently of one another, be substituted by heteroatoms, with the proviso that the at least one odor modulator compound of general formula (V) is not 3-mercapto-1-hexenol (CAS no. unknown), 3-mercapto-3-methyl-1-hexanol (CAS no. 307964-23-4), 3-mercapto-2-methylbutan-1-ol (CAS no. 227456-33-9), 3-mercaptopentan-1-ol (CAS no. 548740-99-4) or 3-mercaptohexan-1-ol (CAS no. 51755-83-0).

7. The liquid composition according to claim 1, wherein the microcapsules are core/shell microcapsules.

8. The liquid composition according to claim 1, wherein the microcapsules have a semipermeable shell, and the capsule core comprises at least 50 wt. % of the at least one odor modulator compound, and the microcapsules and the capsule core are free of odorants.

9. The liquid composition according to claim 1, wherein the microcapsules have an impermeable shell, and the core contains at least 70 wt. %, of the at least one odorant.

10. The liquid composition of claim 1, wherein the microcapsules have an average diameter $X_{50.3}$ (volume average) of from 0.1 to 200 μm.

11. The liquid composition according to claim 1, wherein the microcapsules are contained in an amount of from 0.0005 to 0.15 wt. %.

12. The liquid composition according to claim 1, wherein the at least one odor modulator compound is contained in the composition according to the invention in an amount of from 1.5 wt. % to 0.000001 wt. %, in each case based on the total of all the odorants contained in the composition.

13. The liquid composition according to claim 1, further comprising at least one surfactant, selected from anionic, cationic or nonionic surfactants.

14. The liquid composition according to claim 1, further comprising at least one thickener.

15. The liquid composition according to claim 1, further comprising at least one inorganic salt.

\* \* \* \* \*